(12) United States Patent
Lynch et al.

(10) Patent No.: US 6,207,397 B1
(45) Date of Patent: Mar. 27, 2001

(54) IN VITRO FLUORESCENCE POLARIZATION ASSAY

(75) Inventors: Berkley A. Lynch, Cambridge; Ian MacNeil, Milton; Mark Zoller, Weston, all of MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/955,650

(22) Filed: Oct. 22, 1997

Related U.S. Application Data

(63) Continuation-in-part of application No. 08/844,152, filed on Apr. 18, 1997.
(60) Provisional application No. 60/029,870, filed on Nov. 6, 1996, and provisional application No. 60/015,590, filed on Apr. 18, 1996.

(51) Int. Cl.[7] .......... G01N 33/53; C07D 255/04; C07D 311/82
(52) U.S. Cl. .......... 435/7.8; 435/7.1; 436/501; 549/223
(58) Field of Search .......... 436/501; 435/7.1, 435/7.8; 549/223

(56) References Cited

U.S. PATENT DOCUMENTS

| | | | |
|---|---|---|---|
| 5,248,791 | * 9/1993 | Brynes et al. | 549/223 |
| 5,352,660 | 10/1994 | Pawson | 514/12 |

FOREIGN PATENT DOCUMENTS

| | | |
|---|---|---|
| WO97/ 08300 | 3/1997 | (WO) . |
| WO97/ 12903 | 4/1997 | (WO) . |

OTHER PUBLICATIONS

Panayotou et al., Mol. Cell. Biol., vol. 13 (6): 3567–3576, 1993.
Rameh et al., Cell, vol. 83: 821–830, 1995.
Kavanaugh et al., Science, vol. 266: 1862–1865, 1994.
Blaikie et al., J. Biol. Chem., vol. 269(51): 32031–32034, 1994.
Bork et al., Cell, vol. 80: 693–694, 1995.

* cited by examiner

Primary Examiner—Hankyel Park
(74) Attorney, Agent, or Firm—David L. Berstein

(57) ABSTRACT

An in vitro assay method permits the identification of a test substance which inhibits the mutual association of two molecules. The method includes the steps of providing two components capable of mutual association, one of said components bearing a covalently linked fluorophore; preparing a mixture containing the two components and at least one test substance; irradiating the mixture with polarized light of a suitable wavelength permitting excitation of the fluorophore as indicated by emission of polarized light; measuring the degree of polarization of the emission, and determining the effect of the presence or concentration of the test substance in decreasing the observed emission polarization of a mixture of the two components alone. Inhibitory activity of the test substance correlates with decreased depolarization values.

11 Claims, 5 Drawing Sheets

$y = (m0) / (m1 + m0)$

|  | Value | Error |
|---|---|---|
| m1 | 2.3793e-07 | 8.0905e-09 |
| Chisq | 0.0026986 | NA |
| R | 0.99875 | NA |

Long Format

Short Format

IN VITRO FLUORESCENCE POLARIZATION ASSAY

This application is a continuation in part of U.S. Ser. No. 08/844,152, filed Apr. 18, 1997 and of U.S. Ser. No. 60/029,870, filed Nov. 6, 1996, both of which are continuations in part of 60/015,590, filed Apr. 18, 1996, the contents of which are incorporated herein by reference.

TECHNICAL FIELD OF THE INVENTION

The invention relates to materials and methods for the identification of inhibitors of intermolecular interactions, especially those involved in cellular signal transduction.

BACKGROUND OF THE INVENTION

Cellular signal transduction, i.e., the series of events leading from extracellular events to intracellular sequelae, is an aspect of cellular function in both normal and disease states. Numerous proteins that function as signal transducing molecules have been identified, including receptors, docking or recruiting proteins and enzymes such as receptor and non-receptor tyrosine kinases, phosphatases and other molecules with enzymatic or regulatory activities. These molecules generally demonstrate the capacity to associate specifically with either proteins or other signaling molecules (e.g. lipids) to form a signaling complex that can alter cell activity.

Signaling proteins often contain domain(s) of conserved sequence, which serve as non-catalytic modules that direct protein-protein interactions during signal transduction. Such domains include among others, SH2, phosphotyrosine interaction ("PI"), WW and SH3 domains. SH2 and PI domains recognize, i.e., bind to, proteins containing characteristic peptide sequences which include one or more phosphorylated tyrosine residues. WW and SH3 domains recognize proteins containing characteristic peptide sequences which need not contain phosphotyrosine residues. Significant information related to such domains, proteins containing them, the production of proteins containing such domains (including protein fragments and fusion proteins), the characteristic peptide sequences which they recognize and the biological and/or clinical role played by the interactions of such proteins has been described in the scientific literature.

In cases in which the interaction of a particular protein molecule with a binding partner is associated with the cause or symptoms of a disease or pathological condition, compounds capable of interfering with that interaction may be useful in preventing or treating the disease or condition in mammals, including human patients.

Critical tools for the discovery of such inhibitors of protein:protein or other intermolecular interactions are binding assays. The well-known two-hybrid interaction/binding assay described by Song and Fields, *Nature*, 340:245–247 (1989) has been used to study the interactions of protein-protein interacting partners [See, Fields et al, U.S. Pat. No. 5,283,173 (Feb. 1, 1994)]. Such approaches have also been used to identify presumed SH2 dependent interactions using yeast [Xing, Z. et al., *Mol. Biol. Cell*, 5:413–421 (1994); and Osborne, M. A. et al., *Biotechnol.*, 13:1474–1478 (1995)] or to detect the inhibition of two-hybrid formation in yeast [Chaudhuri, B. et al., *FEBS Lett.*, 357:221–226 (1995)]. See, also, International patent application No. PCT/US95/03208, incorporated herein by reference for background information on SH3 domains and their ligands including information on the design and preparation of proteins containing various SH3 domains, preparation of peptide ligands for an SH3 domain of interest, and biological/clinical roles of SH3 mediated interactions. See, PCT/US97/02635, incorporated herein by reference, for information on receptor domains (e.g., SH2 and PI domains) for phosphotyrosine-containing ligands, including the design and preparation of proteins containing various SH2 domains, preparation of peptide ligands for an SH2 domain of interest, and biological/clinical roles of SH2-mediated interactions.

Competitive binding assays have been described for detecting test substances which interfere with the association of proteins containing an SH2 domain with their phosphotyrosine containing ligands. See, e.g., Pawson, U.S. Pat. No. 5,352,660. More recently reported binding assays have utilized surface plasmon resonance (Biacore) [see, e.g., Panayotou et al, *Mol. Cell. Biol.*, 13:3567–3576 (1993)] or radioactive ligand based assays. The former has a relatively low throughput, while the latter requires cumbersome filtration manipulations and generates radioactive waste, an increasingly difficult disposal issue.

The availability of materials and methods designed for the rapid and effective identification of inhibitors of protein-:protein interactions would be a boon for drug discovery efforts aimed at a wide variety of target protein mediators. It would permit higher-throughput and more efficient identification and development of new pharmaceutical compositions containing inhibitors of intermolecular interactions linked to undesirable or pathological conditions.

SUMMARY OF THE INVENTION

The present invention addresses this need by providing novel materials and methods for in vitro competitive binding assays for identifying substances which inhibit or interfere with the binding together of pairs of molecules capable of mutual association, i.e., binding, to form binding complexes. Such associations include, among others, protein:protein interactions as described above, protein:lipid interactions (see, for example, Rameh et al, *Cell* 83(5), 821–830 (1995)), or protein:small molecule interactions. One class of small molecules capable of binding to signal transducing molecules, specifically SH2 domains, is described in detail in WO 97/12903.

Of particular interest are assays for identifying compounds capable of inhibiting the binding of intracellular proteins or protein domains, especially those involved in cellular signal transduction with binding partners therefor The binding partner may be a naturally occurring ligand for the protein or protein domain of interest, may be derived from such a natural ligand, or may be a surrogate therefor. Such proteins include, for instance, proteins which contain one or more SH2 domains, PI domains, SH3 domains, or WW domains, each with a respective ligand.

In one aspect, the invention provides an in vitro assay method for identifying a test substance which inhibits the mutual association of two molecules. In a preferred case the two molecules are polypeptides, and in fact, protein:protein embodiments such as are disclosed in detail below are useful for illustrating the general class of intermolecular associations. The method includes the steps of preparing a mixture containing the first protein, the second protein bearing a covalently linked fluorophore, and at least one test substance. The mixture is irradiated with polarized light of a suitable wavelength permitting excitation of the fluorophore as indicated by emission of polarized light. The degree of polarization of the emission is measured and the effect of the presence or concentration of the test substance is determined. Inhibitory activity of the test substance is shown by a decrease in the observed emission polarization values of the mixture of the first and second proteins in the presence of the test substance as compared with the same protein mixture in the absence of the test substance.

Inhibition of protein:protein association can result from binding a test substance to the first protein or to the labeled ligand protein or peptide. Thus, the assay method can be viewed as a method for identifying a test substance which competitively binds to either member of the binding pair. As above, the degree of polarization of the emission is measured, and the effect of the presence or concentration of the test substance in decreasing the observed emission polarization is observed and compared with a mixture in the absence of the test substance. Competitive binding of the test substance correlates with decreased depolarization values.

In still another aspect, the invention provides an inhibitor of the association of a first protein with a second protein, first identified by the methods above.

In yet another aspect, the invention provides components or reagents, e.g., a protein bearing a covalently linked fluorophore, useful in the methods of the invention. One or more of the components or reagents can further be packaged in a kit with instructions for use in the described methods.

Other aspects and advantages of the present invention are described further in the following detailed description of the preferred embodiments thereof.

Figure 6A:
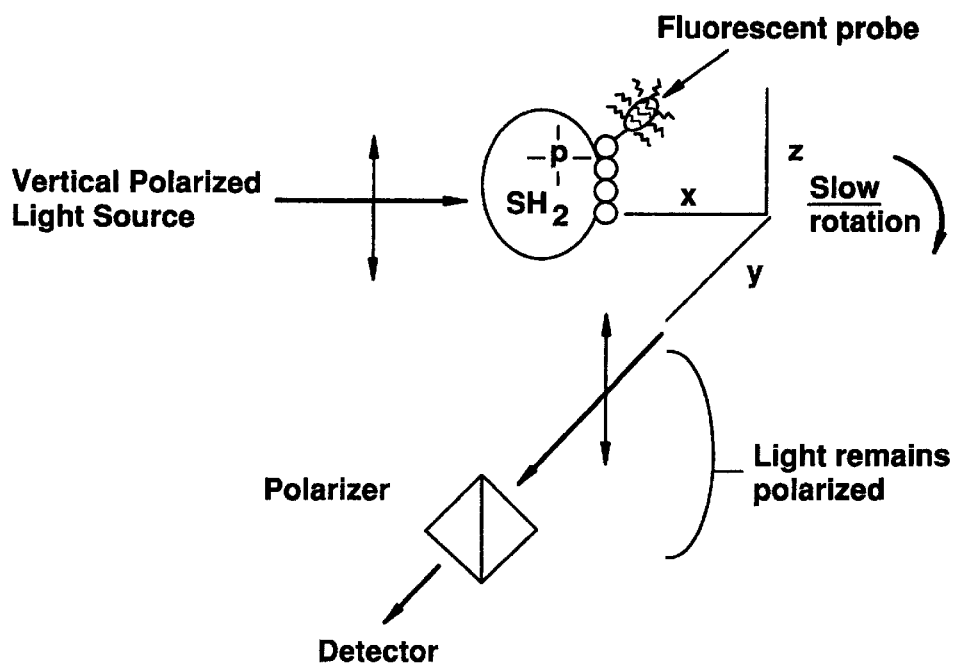
FIG. 6A is a depiction of performance of the FP assay with no inhibitor present. In this figure, the fluorescein-labeled second protein (or probe) binds to its binding partner (first protein having an SH2 domain). Light from the vertical polarized light source remains polarized due to the slow rotation of the bound complex.
Figure 6B:
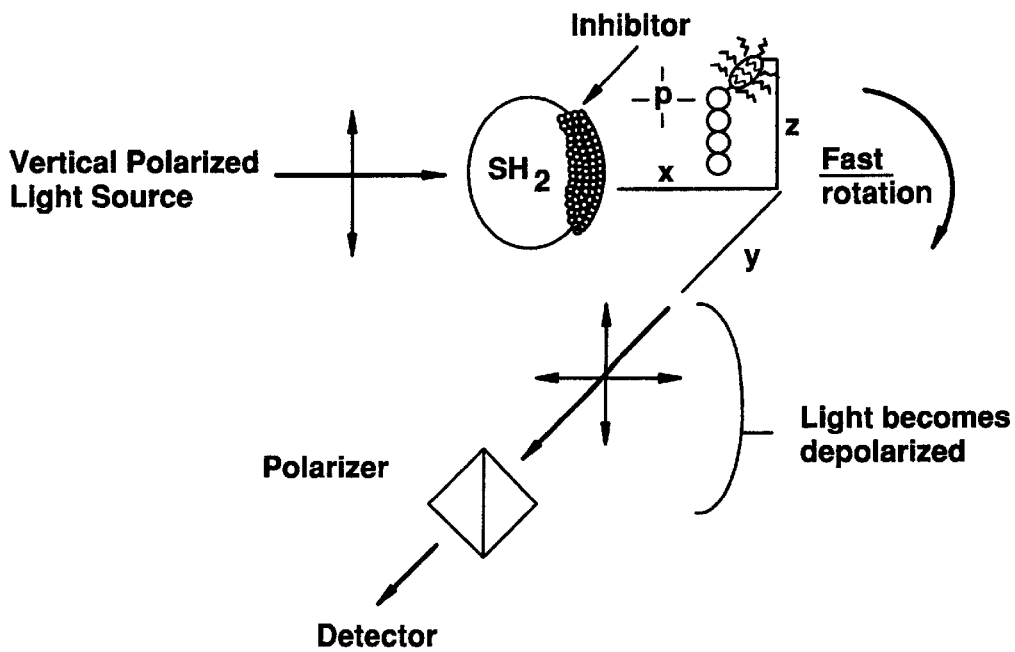
FIG. 6B is a depiction of performance of the FP assay with inhibitor present. In this figure, the inhibitor binds to the SH2 domain-containing first protein, thereby preventing binding of the fluorescein-labeled second protein (or probe).

The small unbound probe rotates more quickly than does the complex of FIG. 6A. Light from the vertical polarized light source becomes depolarized due to the quick rotation of the unbound probe.

DETAILED DESCRIPTION OF THE INVENTION

Various binding assays and methods have been designed for determining the presence and/or concentration in biological fluids of a known substance of interest, e.g. a therapeutic drug, a metabolite thereof, an illicit drug, etc. The present invention addresses a different problem: the identification of a substance, of known or unknown structure, which inhibits the intermolecular association of two assay components, typically a protein and either a protein or non-protein ligand therefor. Said differently, this invention provides a method and materials for characterizing the ability of a test substance (of known or unknown structure) to inhibit the previously mentioned intermolecular association. Our invention does so by providing a fluorescence polarization (FP)-based assay for identifying and measuring the capacity of a test substance to disrupt or inhibit the association between a pair of molecules, e.g. proteins. The novel assay methods and materials disclosed herein have the advantages of being robust, non-radioactive, and amenable to varying degrees of automation.

COMPONENTS OF THE ASSAY

To facilitate understanding of this invention, the following descriptions of the components of the assay are provided:

A. The Intemiolecular Interaction

The assay of the present invention is designed to enable one to detect an inhibitor of any intermolecular interaction. By the terms "intermolecular interaction" or "mutual association" of molecules is meant any complex or binding, covalent or non-covalent, which naturally forms between two molecules. One example of a protein:protein association involves the complex formed between a receptor and its naturally-occurring ligand. Interactions between fragments of proteins, i.e., peptides, with another protein or peptide are also encompassed by the term protein:protein interaction, and the terms "protein", "peptide" and "polypeptide" are used here interchangeably. Examples of protein:protein binding abound in the art, e.g., the binding between an antibody and a protein antigen or epitope, the binding between a cell-surface receptor and its protein ligand, the binding of various signalling proteins with their protein binding pairs, etc.

Specific examples of a protein:protein interaction, which are used herein to demonstrate the method of this invention involve, as a first protein, a protein containing one or more SH2 domains, and/or SH3 domains (Syk, Zap, Src and Lck) and, as a second protein, a ligand for that first protein. For additional background information on Zap and Syk proteins and their SH2 domains, and peptide ligands, see, International Patent Application Nos. PCT/US96/13918, incorporated herein by reference. For non-protein ligands for SH2 domains, se e.g. WO 97/12903 (Lunney et al.).

The invention encompasses embodiments in which the first molecule comprises a single binding domain for a ligand (e.g. an SH2 domain and an SH2 ligand). It also encompasses embodiments in which the first molecule comprises two or more binding domains (e.g. two SH2 domains, or an SH2 domain and an SH3 domain) and is used with a separately labeled ligand for each such domain or a "composite" ligand, naturally occuring or otherwise, which binds to the first molecule, presumably through two or more of the binding domains.

B. The First Protein/Peptide Molecule of the Binding Pair

For the purposes of the present invention, and for using currently conventional detection equipment, it is preferred to use a first protein/peptide that has a significantly greater molecular weight than the second protein, peptide or other ligand therefor, which naturally interacts with it. For purposes of this invention, the larger protein which participates in the intermolecular interaction is referred to as the first protein. It is the ligand for that protein which is labelled with the fluorophore according to the assay method. Generally, the larger protein of the binding pair has a molecular weight of at least 2 to about 100 times greater than the molecular weight of its labeled ligand. Often, the first protein of the binding pair has a molecular weight of at least 25 to about 50 times greater than the molecular weight of the labeled ligand.

The first protein need not necessarily be rigorously purified in production, as described below, but it is important to know the concentration of the first protein for certain quantitative purposes, e.g., for the construction of a saturation curve or to determine Kd values for the affinity of the two protein components.

One specifically exemplified "first protein" of the examples contains an SH2 domain which serves as a receptor for a tyrosine phosphorylated peptide. Such a receptor may be a protein, a fusion protein, polypeptide, peptide or fragment thereof which contains a "phosphopeptide binding domain" (PBD). A PBD is a receptor domain present, e.g., in certain signaling proteins, which is capable of binding to a phosphorylated protein or phosphopeptide and thereby of directing protein-protein or protein-peptide association. For example, an "SH2 domain" is one such receptor domain. The receptor can be a polypeptide containing one or more SH2, or other phosphopeptide binding domains. The receptor may be located within a larger protein, or may be a peptide fragment thereof. The receptor is preferably of human or other animal origin.

Numerous proteins containing such receptors (e.g., SH2 domains, PI domains, etc.) are known. See, e.g., U.S. Pat. No. 5,352,660.

Another specifically exemplified "first protein" contains an SH3 domain which serves as a receptor for a corresponding peptide sequence or motif. Such a receptor may be a protein, a fusion protein, polypeptide, peptide or fragment thereof which contains an SH3 or SH3-like domain.

Another specifically exemplified "first protein" contains both an SH2 and an SH3 domain.

C. The Second Component of the Binding Pair

The second component is a ligand (naturally-occurring or otherwise) of the first protein or receptor. The second component is generally the smaller of the components of the binding pair and is preferably the component of the pair which is labeled with a fluorescent moiety, thereby forming the "probe" component useful in the methods described herein.

In one example where the first protein contains an SH2 domain, the second component or "ligand" is a protein, fusion protein, peptide or fragment thereof which contains one or more tyrosine residues, which is capable of binding selectively and with specificity to a phosphopeptide binding domain when at least one of the peptide ligand's tyrosine residues is phosphorylated. Alternatively, such "SH2 ligands" may be polypeptides containing a phosphate mimic such as a phosphonate (see WO 97/08300) or any other substance which binds an SH2 domain of interest with appropriate affinity and can be labeled with a fluorophore (see WO 97/12903).

Considerable information on the sequence specificity of peptide ligands for receptors, e.g., SH2, SH3, PI, and WW domains, etc. is also known. When it is used as a probe in the assay of this invention, this ligand is labeled with a suitable fluorophore as discussed in more detail below. Typically, a probe peptide or protein or other ligand binds to its (usually) larger binding partner with a Kd in the range of about 0.1 to about 1000 nM. More desirably, the two binding partners bind to each other with a Kd better than (i.e., numerically smaller than) about 300 nM, more preferably with a Kd in the range of about 5 to about 50 nM.

D. Methods of Producing the First and Second Proteins/Peptides of the Binding Pair DNA sequence information and expression technology is available which permits recombinant production of any desired protein(s)/peptide(s) using a variety of expression systems. To produce proteins used in these assays, one may express DNAs encoding the whole protein or a portion of the protein containing at least a domain of interest. The protein or portion of the protein may be expressed as a fusion protein, also by conventional techniques, especially in the case of the larger of the two binding proteins.

Any materials and methods conventional for producing a protein may be used including both prokaryotic and eukaryotic systems. For example, such proteins/peptides may be expressed by baculovirus, bacterial, yeast or mammalian expression systems, whether as full-length proteins, fragments containing the receptor domain(s) or as fusion proteins. Such expression systems are conventional in the art. See, for examples, the descriptions in Sambrook et al, *Molecular Cloning. A Laboratory Manual.*, 2d edit., Cold Spring Harbor Laboratory, NY (1989).

The use of conventional protein/peptide expression technology permits the production of any interacting protein pair of any size. The expression systems and the conventional components thereof used to express the protein components of this invention are well within the skill of the art and do not limit the scope of this invention.

By way of illustration, expression vectors for a protein or domain of interest can be constructed by ligating into a conventional expression vector the DNA sequence encoding the desired protein, protein domain or, if known, a consensus homology domain for the domain of interest, alone or preferably with additional flanking sequence. With routine experimentation, one can determine, if desired, whether such additional flanking amino acids enhance stability, improve expression levels, improve its ability to interact with ligands or other proteins or be necessary or desirable for linking to a fusion protein for reasons discussed below. For example, for human Src the SH3 consensus homology domain includes amino acids 91–140. We have prepared SH3 domain protein from *E. coli* expression vectors using amino acids 84–145, which contain an additional 7 amino acids on the N-terminal side of the homology domain and 5 amino acids on the C-terminal side.

The desired protein or protein domain may be expressed within all or part of its natural context, as an isolated domain, in a tandem array containing two or more of the same or different domains, or as a fusion protein with other unrelated domains including but not limited to SH2-like domains, protein kinase domains, glutathinone S-transferase (GST), epitope tags, kinase recognition sequences, maltose binding protein, signal sequences, biotin-modification sequences, etc.

The proteins or protein domains may be modified to:

facilitate purification e.g. by expression as a fusion to glutathione-S-transferase, maltose binding protein, metal-chelation sequences (poly-histidine), protein A or others;

facilitate identification or quantitation, e.g. by covalent modification using biotin, fluorophores, chromophores, scintillons, spin labels, radioactive or non-radioactive isotope tags, magnetic particles, metal coloids, etc.;

adhere to defined solid supports, e.g. by expression as a fusion to an epitope tag or other antigenic domain; engineered to provide unique or uniquely accessible protein features e.g. N-terminal serine, cysteine, lysine or others, etc.;

remove undesirable features that pose experimental complications, e.g. by mutation of cysteines that participate in unnatural domain dimerization;

improve stability under conditions of binding assays (e.g. by altering the natural coding sequence to encode cysteines that form stabilizing disulfides).

E. The "Test Substance"

A "test substance or inhibitor" is defined herein as a compound or composition which binds selectively to either of the two components, e.g. proteins, which participate in the intermolecular interaction. Alternatively, the test substance selectively blocks or otherwise inhibits the interaction between these two components. For example, this inhibitor can bind to the first protein with competitive avidity vis-a-vis its naturally occurring binding protein, or it can bind the second component. Where the two components are exemplified as a tyrosine phosphorylated receptor and its naturally occurring ligand, the inhibitor can bind to the receptor competitively with the ligand, or it can selectively block or otherwise inhibit the interaction between the receptor and ligand normally mediated by one or more tyrosine phosphorylated peptides or domains.

Test substances or compositions to be assessed for their ability to bind selectively to the first or second protein of interest can be obtained from a variety of sources, including, for example, microbial broths, cellular extracts, conditioned media from cells, synthetic compounds and combinatorial libraries. The assay method of this invention may be used to screen natural product and test compound libraries or structurally-biased diversity libraries to identify desired inhibitors. The test substance may be selected from a mixture of one or more test peptides, wherein said mixture is provided in the form of a library of synthetic peptides or in the form of a phage library displaying the various peptides.

F. A "Fluorescent Moiety"

A "fluorophore" or "fluorescent moiety" is a fluorescent molecule which, in solution and upon excitation with polarized light, emits light back into a fixed plane (i.e., the light remains polarized). Numerous known fluorescent labeling moieties of a wide variety of structures and characteristics are suitable for use in the practice of this invention. Similarly, methods and materials are known for covalently linking them to other molecules [see, e.g., Richard P. Haugland, Molecular Probes: Handbook of Fluorescent Probes and Research Chemicals 1992–1994 (5th edit, 1994, Molecular Probes, Inc.)]. In choosing a fluorophore, it is preferred that the lifetime of the fluorophore's exited state be long enough, relative to the rate of motion of the labeled probe or peptide, to permit measurable loss of polarization following emission. Suitable fluorophores include fluorescein, fluorescein isothiocyanate, rhodamine, dichlorotriazinylamine fluorescein, dansyl chloride, phycoerythrin, and umbelliferone.

It is typically preferred to use a fluorophore having an excitation wavelength and emission wavelength in the visible rather than ultraviolet range of the spectrum to avoid possible interference from test compound fluorescence. Preferably the fluorophore is covalently linked to the smaller protein, i.e., the second protein, to be labeled, e.g., a peptide ligand, using a sufficiently short linker to avoid introducing undue motion to the fluorophore, i.e., motion not correlated to the motion of the labelled peptide.

More specifically, the examples below provide a description of the method used by these inventors in which a fluorescent moiety is chemically attached by covalent bonds onto a second protein molecule (a peptide ligand). In Example 2, the phospho-Tyr containing peptide is labelled with fluorescein in vitro. One of skill in the all will understand that any method of production of such phosphopeptides or their mimics is applicable.

G. "Fluorescence Polarization"

FP, first described by Perrin, *J. Phys. Rad.*, 1:390–401 (1926), is based upon the finding that the emission of light by a fluorophore can be depolarized by a number of factors, the most predominant being rotational diffusion, or, in other words, the rate at which a molecule tumbles in solution. "Polarization" is the measurement of the average angular displacement of the fluorophore which occurs between the absorption and subsequent emission of a photon. This angular displacement of the fluorophore is, in turn, dependent upon the rate and extent of rotational diffusion during the lifetime of the excited state, which is influenced by the viscosity of the solution and the size and shape of the diffusing fluorescent species. If viscosity and temperature are held constant, the polarization is directly related to the molecular volume or size of the fluorophore. In addition, the polarization value is a dimensionless number (being a ratio of vertical and horizontal fluorescent intensities) and is not affected by the intensity of the fluorophore.

F. Additional Information Relating to Illustrative Signal Transducing Domains of Particular Interest (i) SH2 or SH2-like Domains The term "SH2 domain" refers to a sequence which is substantially homologous to a Src homology region 2 (SH2 region). The Src homology region 2 is a noncatalytic domain of ~100 amino acids which was originally identified in the viral Fps and viral Src cytoplasmic tyrosine kinases by virtue of its effects on both catalytic activity and substrate phosphorylation (T. Pawson, Oncogene 3, 491 (1988) and I. Sadowski et al., Mol. Cell. Biol. 6, 4396 (1986)). SH2 domains have been found in a variety of eukaryotic proteins, some of which function in intracellular signal transduction. Many are known in the art. Examples (including counterparts from various species) of SH2 domain-containing proteins include (1) members of the src-family protein tyrosine kinases (Src, Lyn, Fyn, Lck, Hck, Fgr, Yes), (2) Shc (3) Tsk, (4) Btk, (5) VAV, (6) Grb2, (7) Crk, and (8) signal transducer and transcription (STAT) proteins. In addition, a number of proteins, such as ZAP-70, p85 phosphatidylinositol 3' kinase (PI3K), Syk, GTPase Activating Protein (GAP), and Phospholipase C gamma, have two SH2 domains. SH2 domain-containing proteins have been identified in human, rodent, sheep, bovine, C. elegans, Drosophila, Xenopus, flatworm, freshwater sponge, and hydra.

One way to identify new SH2 or SH2-like domains from unknown DNA, RNA or protein sequence is by using one of many available computer alignment programs. One example is pfscan, which can be run via the World Wide Web (WWW) site at http://ulrec3.unil.ch/software/profilescan.html. To use the program, a protein sequence is tested against a "profile" describing the SH2 domain motif. According to the program information, the particular strength of profiles is that they can be used to describe very divergent protein motifs. These profiles are normally derived from multiple alignments of the initial sequence set. In addition to the sequences themselves, a profile identifies which types of residues are allowed at what position within the domain, which amino acids are conserved, which ones are not, which positions or regions can allow insertions, and which regions may be dispensable. Additional information on Pfscan and PROSITE can be obtained at the web page http://ulrec3.unil.ch/index.html operated by the Bioinformatics Group at the ISREC (Swiss Institute for Experimental Cancer Research).

As an example we analyzed the peptide sequence of human Src with the pfscan program. The results are shown below. The program clearly identified the SH2 domain of Src as encompassing the region from amino acids 150–247 of the Src peptide sequence. In addition, the SH3 and kinase domains were identified by pfscan.

| NScore | raw | from-to | Profile | Description |
|---|---|---|---|---|
| 26.9695 | 1792 | pos. 150–247 | PS50001 | SH2 Src homology 2 (SH2) domain |
| 20.2947 | 1182 | pos. 83–144 | PS50002 | SH3 Src homology 3 (SH3) domain |
| 43.4246 | 2912 | pos. 269–522 | PS50011 | PROTEIN_KINASE_DOM Protein kinase |

The NScore of a match is the negative decadic logarithm of the expected number of matches of the given quality (or better) in a random database of the given size. For NScores <<1 this converges to the probability of finding the match in the database. Since the number of expected matches depends on the size of the database, the decadic logarithm of the database size must be subtracted before the calculation:

$$-\log(NExp) = NScore - \log(DBsize)$$

where (NExp=Expected number of chance matches) and (DBsize=size of the database in characters).

The following table gives somes examples on how to convert the NScores into probabilities for the SwissProt database and the nonredundant (nr) protein database. The calculation is based on a database size of 18,531,385 residues for SwissProt (log=7.27)

58,154,119 residues for the nr database (log=7.76)

Expected chance matches in:

| NScore | SwissProt | nonredundant |
|---|---|---|
| 7.0 | 1.8 | 5.8 |
| 7.5 | 0.58 | 1.82 |
| 8.0 | 0.18 | 0.58 |
| 8.5 | 0.058 | 0.182 |
| 9.0 | 0.018 | 0.058 |
| 9.5 | 0.006 | 0.0182 |
| 10.0 | 0.0018 | 0.0058 |
| 10.5 | 0.0006 | 0.0018 |
| ... and so on ... | | |

The segment of a test sequence contains an SH2 domain with an SH2 profile NScore value >7.5, preferably >8, more preferably >9, more preferably >10.

As a second example, the N-terminal 160 amino acid sequence from human ZAP-70 was applied to pfscan. The result indicated an SH2 domain bounded by amino acids 10–102.

| NScore | raw | from-to | Profile | Description |
|---|---|---|---|---|
| 16.4402 | 1082 | pos. 10–102 | PS50001 | SH2 Src homology 2 (SH2) domain |

SH2 domains can be identified using other computer alignment programs, such as MegAlign within the DNAstar computer package (Madison, Wis.). To do this, one or more known SH2 domains and a test sequence are aligned by the clustal method. A sequence having 3 25%, in some cases 30–50%, in other cases >50%, amino acids identical to a known SH2 domain is identified as an SH2 homology domain. The positions of identical amino acids between the test sequence and different known SH2 domains can vary, except for one position. All SH2 domains identified to date have a conserved arginine residue approximately 25–40 residues from the start of the SH2 homology domain. In human src this arginine is found within the sequence FLVRES, where abbreviations for the amino acid residues are: F, Phe; L, Leu; V, Val; R, Arg; E, Glu; S, Ser.

Another way to identify SH2 or SH2-like domains is by running a query in the federated nucleotide or protein databases for the SH2 domain feature. In the SWISS-PROT database, this is listed under the FT or "feature" heading. SWISS-PROT database can be accessed over the WWW at EBI http://www.ebi.ac.uk. For example, in the file listed for human Src (P12931), the region containing the SH2 domain is shown to be 150–247.

```
SWISS-PROT: P12931
ID     SRC_HUMAN       STANDARD;     PRT;      535 AA.
AC     P12931;
DR     MIM; 190090; —.
DR     PROSITE; PS00107; PROTEIN_KINASE_ATP.
DR     PROSITE; PS00109; PROTEIN_KINASE_TYR.
DR     PROSITE; PS50001; SH2.
DR     PROSITE; PS50002; SH3.
DR     PROSITE; PS50011; PROTEIN_KINASE_DOM.
DR     PRODOM [Domain structure/List of seq. sharing at least
       1 domain]
DR     SWISS-2DPAGE; GET REGION ON 2D PAGE.
KW     TRANSFERASE; TYROSINE-PROTEIN KINASE;
       PROTO-ONCOGENE;
PHOSPHORYLATION;
KW     ATP-BINDING; MYRISTYLATION; SH3 DOMAIN; SH2
       DOMAIN.
FT     INIT_MET        0     0   BY SIMILARITY.
FT     LIPID           1     1   MYRISTATE (BY SIMILARITY).
FT     DOMAIN         83   144   SH3.
FT     DOMAIN        150   247   SH2.
FT     DOMAIN        269   522   PROTEIN KINASE.
FT     NP_BIND       275   283   ATP (BY SIMILARITY).
FT     BINDING       297   297   ATP (BY SIMILARITY).
FT     ACT_SITE      388   388   BY SIMILARITY.
FT     MOD_RES       419   419   PHOSPHORYLATION (AUTO-)
                                 (BY SIMILARITY).
FT     MOD_RES       529   529   PHOSPHORYLATION
                                 (BY SIMILARITY).
```

Yet another way to identify SH2 or SH2-like domains may be accomplished by screening a cDNA expression library with a phosphorylated peptide ligand for a known SH2 domain to isolate cDNAs for SH2 proteins. One could use PCR or low stringency screening with an SH2-specific probe. The SH2 domain or protein containing the SH2 domain may be isolated from naturally occuring sources (e.g. cells, tissues, organs, etc); produced recombinantly in bacteria, yeast or eukaryotic cells; produced in vitro using cell free translation systems; or produced synthetically (e.g. peptide synthesis).

The alignment of SH2 domains used to generate the SH2 profile for pfscan, as taken from http://ulrec3.unil.ch/prf_details/alignments/SH2.msf (profile matrix can be obtained from http://ulrec3.unil.ch/cgi-bin/get_pstprf?SH2) is based on alignment of approximately 390 SH2 domains from proteins of various species. The list of proteins containing SH2 domains used in the alignments in the Swiss-Prot Database includes the following (P##### is the Swiss-Prot Database Accession number):

| | | |
|---|---|---|
| P00519, ABL1_HUMAN | P00520, ABL_MOUSE | P00521, ABL_MLVAB |
| P00522, ABL_DROME | P00523, SRC_CHICK | P00524, SRC_RSVSR |
| P00525, SRC_AVISR | P00526, SRC_RSVP | P00527, YES_AVISY |
| P00528, SRC1_DROME | P00530, FPS_FUJSV | P00541, FPS_AVISP |
| P00542, FES_FSVGA | P00543, FES_FSVST | P00544, FGR_FSVGR |
| P03949, ABL1_CAEEL | P05433, GAGC_AVISC | P05480, SRCN_MOUSE |
| P06239, LCK_HUMAN | P06240, LCK_MOUSE | P06241, FYN_HUMAN |
| P07332, FES_HUMAN | P07947, YES_HUMAN | P07948, LYN_HUMAN |
| P08103, HCK_MOUSE | P08487, PIP4_BOVIN | P08630, SRC2_DROME |
| P08631, HCK_HUMAN | P09324, YES_CHICK | P09769, FGR_HUMAN |
| P09851, GTPA_BOVIN | P10447, ABL_FSVHY | P10686, PIP4_RAT |
| P10936, YES_XENLA | P12931, SRC_HUMAN | P13115, SRC1_XENLA |
| P13116, SRC2_XENLA | P13406, FYN_XENLA | P14084, SRC_AVISS |
| P14085, SRC_AVIST | P14234, FGR_MOUSE | P14238, FES_FELCA |
| P15054, SRC_AVIS2 | P15498, VAV_HUMAN | P16277, BLK_MOUSE |
| P16333, NCK_HUMAN | P16591, FER_HUMAN | P16879, FES_MOUSE |
| P16885, PIP5_HUMAN | P17713, STK_HYDAT | P18106, FPS_DROME |
| P19174, PIP4_HUMAN | P20936, GTPA_HUMAN | P23615, SPT6_YEAST |
| P23726, P85B_BOVIN | P23727, P85A_BOVIN | P24135, PIP5_RAT |
| P24604, TEC_MOUSE | P25020, SRC_RSVH1 | P25911, LYN_MOUSE |
| P26450, P85A_MOUSE | P27446, FYN_XIPHE | P27447, YES_XIPHE |
| P27870, VAV_MOUSE | P27986, P85A_HUMAN | P29349 CSW_DROME |
| P29350, PTN6_HUMAN | P29351, PTN6_MOUSE | P29353, SHC_HUMAN |
| P29354, GRB2_HUMAN | P29355, SEM5_CAEEL | P31693, SRC_RSVPA |
| P32577, CSK_RAT | P34265, YKF1_CAEEL | P35235, PTNB_MOUSE |
| P35991, BTK_MOUSE | P39688, FYN_MOUSE | P40763, STA3_HUMAN |
| P41239, CSK_CHICK | P41240, CSK_HUMAN | P41241, CSK_MOUSE |
| P41242, CTK_MOUSE | P41243, CTK_RAT | P41499, PTNB_RAT |
| P42224, STA1_HUMAN | P42225, STA1_MOUSE | P42226, STA2_HUMAN |
| P42227, STA3_MOUSE | P42228, STA4_MOUSE | P42229, STA5_HUMAN |
| P42230, STA5_MOUSE | P42231, STA5_SHEEP | P42232, STAB_MOUSE |
| P42679, CTK_HUMAN | P42680, TEC_HUMAN | P42681, TXK_HUMAN |
| P42682, TXK_MOUSE | P42683, LCK_CHICK | P42684, ABL2_HUMAN |
| P42685, FRK_HUMAN | P42686, SRK1_SPOLA | P42687, SPK1_DUGTI |
| P42688, SRK2_SPOLA | P42689, SRK3_SPOLA | P42690, SRK4_SPOLA |
| P43403, ZA70_HUMAN | P43404, ZA70_MOUSE | P43405, SYK_HUMAN |
| P46108, CRK_HUMAN | P46109, CRKL_HUMAN | Q00655, SYK_PIG |
| Q02977, YRK_CHICK | Q03526, ITK_MOUSE | Q04205, TENS_CHICK |
| Q04736, YES_MOUSE | Q04929 CRK_CHICK | Q05876, FYN_CHICK |
| Q06124, PTNB_HUMAN | Q06187, BTK_HUMAN | Q07014, LYN_RAT |
| Q07883, GRB2_CHICK | Q08012, DRK_DROME | Q08881, ITK_HUMAN |

Certain SH2 or SH2-like domains may not be identified via the pfscan program nor exhibit significant homology with known SH2 domain sequences to be detected by computer alignment programs. These sequences may, nevertheless, exhibit the same or similar three-dimensional structure as known SH2 domains and function as an SH2-like domain and function to bind phosphotyrosine-containing peptides or proteins. The three-dimensional structure of several known SH2 domains have been determined. SH2 domains are characterized as two anti-parallel beta sheets composed of 5 or 6 beta strands. Regions forming an alpha helix may or may not be present within the domain. SH2 or SH2-like domains may be recognized as having an SH2-like domain structure when solved by x-ray crystallography or NMR spectroscopy. Alternatively, a predicted structure by homology modeling may be used to identify a particular protein sequence as an SH2-like domain.

A general method to identify an SH2 domain within a test peptide or nucleotide sequence follows:

1. Translate the cDNA or RNA into single letter code protein sequence. This could be accomplished using a computer program such as DNA strider or EditSeq in the DNAstar package.
2. Go to the WWW site at http://ulrec3.unil.ch/software/profilescan.html
3. Copy the test sequence into the appropriate box in the pfscan form
4. Submit the form to the pfscan server
5. The results are sent back through the web browser or via e-mail.

SH2 and SH2-like domains as described in the foregoing paragraphs may be used in the practice of this invention. Using information provided herein, and by analogy to the examples provided below, one may carry out this invention with any SH2 domain, SH2-like domain, PID or PID-like domain and a peptide ligand therefor, e.g. in place of ZAP, Syk, Src or Fyn SH2 domains.

(ii) PID or PID-like Domains

An alternative phosphotyrosine binding domain to SH2 domains is the so-called phosphotyrosine interaction domain (PID). This domain, containing on average about 160 amino acid residues, was originally identified in the Shc protein. In contrast to SH2 domains, which recognize sequences having a consensus pTyr-Xaa-Xaa-Xaa-Xaa (a phosphotyrosine followed by three or more amino acids), PID domains recognize sequences with the consensus Asn-Xaa-Pro-pTyr (also called NPXY in single letter code). The invention described in this application is also relevant to PID and PID-like domains. In this case, the coding sequence for a PID domain is substituted in the appropriate vector for the SH2 domain coding sequence and a ligand that recognizes the PID domain replaces the SH2 domain ligand. Phosphorylation of the PID ligand could be accomplished using v-Src, as described herein. Alternative protein kinases could be used to phosphorylate the PID ligand. In addition, a protein kinase endogenous within the cell could catalyze phosphorylation of the PID ligand.

Significant information concerning these domains is known in the art. A detailed description of the PID domains can also be found on the WWW at the site http://www.bork.embl-heidelberg.de/Modules/pid-gif.html. The following information is taken from that site:

Documentation—PROSITE description

Beside SH2, the phosphotyrosine interaction domain (PI domain or PID)[3] is the second phosphotyrosine-binding domain found in the transforming protein Shc [1,2]. Shc couples activated growth factor receptors to a signalling pathway that regulates the proliferation of mammalian cells and it might participate in the transforming activity of oncogenic tyrosine kinases. The PI domain specifically binds to the Asn-Pro-Xaa-Tyr(p) motif found in many tyrosine-phosphorylated proteins including growth factor receptors. PID has also been found in the Shc related protein Sck [1] and several otherwise unrelated regulatory proteins [3] which are listed below.

Mammalian Shc (46 kD and 52 kD isoforms) contains one N-terminal PID, a collagen-like domain and a C-terminal SH2 domain.

Human Shc related protein Sck contains one PI domain and a SH2 domain.

Mammalian X11 is expressed prominently in the nervous system. It contains 2 disc homologous regions (DHR) of about 100 AA downstream of the PID.

Drosophila nuclear Numb protein is required in determination of cell fate during sensory organ formation in drosophila embryos. It has one PID.

Caenorhabditis hypothetical protein F56D2.1 contains an N-terminal metalloproteinase domain followed by one PID.

Rat FE65. The WW domain as well as the 2 PIDs found in the sequence of FE65 indicate that this protein is probably involved in signal transduction.

Drosophila protein disabled is a cytoplasmic, tyrosine phosphorylated protein found in CNS axons and body wall muscles. It is involved in embryonic neural development. It contains one N-terminal PI domain.

Mouse mitogen responsive phosphoprotein isoforms P96, P93 and P67 which are produced by alternative splicing, contain one N-terminal PID. This is also true for the differentially expressed human ortholog Doc-2.

Human EST05045 protein fragment has one PID.

References:

[1] Kavanaugh W. M., Williams L. T. Science 266:1862–1865(1994)

[2] Blaiki, P. et al., J.Biol.Chem. 269, 32031–32034 (1994)

[3] Bork P., Margolis B. Cell 80, 693 (1995)

A PI domain alignment based on a number of PI domains from various species is illustrated in the WWW site at http://ulrec3.unil.ch/prf_-details/alignments/PID.msf. Another such alignment is shown at the web site at http:H/www.bork.embl-heidelberg.de/Modules/pi-ali.html.

(iii) SH3 and SH3-like domains

The term "SH3-like domain" refers to a sequence which is substantially homologous to a Src homology region 3 (SH3 region). The Src homology 3 region is a noncatalytic domain of ~60 amino acids which was originally identified in the viral Fps and viral Src cytoplasmic tyrosine kinases by virtue of its effects on both catalytic activity and substrate phosphorylation (T. Pawson, Oncogene 3, 491 (1988) and I. Sadowski et al., Mol. Cell. Biol. 6, 4396 (1986)). SH3 domains have been found in a variety of eukaryotic proteins, some of which function in intracellular signal transduction. Examples (including counterparts from various species) of SH3 domain-containing proteins include (1) members of the src-family protein tyrosine kinases (Src, Lyn, Fyn, Lck, Hck, Fgr, Yes), (2) Grb-2, which has two SH3 domains, (3) Sprk, a threonine/serine protein kinase, (4) Tsk, (5) Btk, (6) Vav, (7) GTPase Activating Protein (GAP), (8) p40, p47, and p67 proteins of the neutrophil oxidase complex, and (9) phosphatidylinositol 3' kinase, (10) Crk, (11) phospholipase C gamma, (12) Abl. SH3 domain-containing proteins have been identified in human, rodent, bovine, C. elegans, and yeast. Other SH3 domains may be selected from the scientific literature or identified by sequence analysis or cloning by the methods described above. See e.g. PCTJUS95/03208 for a wealth of background information relating to SH3 domains and their ligands.

Certain SH3 or SH3-like domains may not match any of the 18 conserved amino acids nor exhibit significant homology with known SH3 domain sequences to be detected by computer alignment programs. These sequences may, nevertheless, exhibit the same or similar three-dimensional structure as known SH3 domains and function as an SH3-like domain. The three-dimensional structure of several known SH3 domains have been determined. SH3 domains are characterized as two anti-parallel beta sheets composed of 5 or 6 beta strands. Regions forming an alpha helix may or may not be present within the domain. SH3 or SH3-like domains may be recognized as having an SH3-like domain structure when solved by x-ray crystallography or NMR spectroscopy. Alternatively, a predicted structure by homology modeling may be used to identify a particular protein sequence as an SH3-like domain.

(iv.) Significant amounts of information on other protein and non-protein components of intermolecular interactions are known and may be similarly employed by the practitioner of the subject invention.

II. THE ASSAY PROTOCOL

The in vitro assay method of this invention utilizes FP for identifying a test substance which competitively binds to, or inhibits the mutual association of, a first protein molecule to a second protein molecule. Fluorescence polarization is an extremely useful method for studying ligand-protein and protein-protein interaction. The present invention is based upon the observation that changes in polarization will occur if a fluorescent molecule undergoes a molecular weight change due to cleavage or binding to another molecule. Fluorophores that are of a low-molecular weight, and/or are very flexible, have low polarization values, while those that have a high molecular weight, and/or are rigid, have higher polarization values.

This intrinsic property of the fluorescent moiety is utilized in the assay of this invention. According to this method, a mixture is made which contains the following components:

(a) a selected amount of a first protein molecule, e.g., a tyrosine phosphorylated receptor, which is capable of binding or otherwise mutually associating with a smaller second protein molecule;

(b) a selected amount of a smaller, second protein molecule, which is covalently linked to, or labeled with, a fluorophore. In the examples below, it is the peptide ligand that is labelled with a fluorophore by covalent linkage, thereby forming fluorophore-labeled probes of low molecular weight; and (c) a selected, potentially competitively-inhibiting test substance.

This mixture is accomplished under conditions suitable to permit complex formation between the first and second proteins, if they were admixed in the absence of test substance. Thus, according to this method, in the event that the test substance is, in fact, an inhibitor of the protein:protein complex formation, the conditions are also suitable to permit its competitive binding to the first or second proteins.

This mixture of (a), (b) and (c) is irradiated with plane polarized light of a wavelength which is sufficient to excite the fluorophore. The light subsequently emitted by the fluorescent second protein is polarized to varying degrees depending on the molecular volume of the fluorescent second protein. In the unbound state in solution, low molecular weight peptides rotate rapidly, and give low polarization readings.

When in the presence of its binding/interacting first protein partner, e.g., a receptor, the lower-molecular weight fluorescent second protein binds to the higher molecular weight first protein, e.g., a tyrosine phosphorylated protein or peptide receptor. When the labeled second protein binds to its target first protein and is illuminated by plane polarized light, the large first protein:second protein complex tumbles more slowly, and the polarization readings increase. The method of this invention thus follows changes in the ratio of polarization in the horizontal and vertical planes of the emission wavelength range. This is in distinct contrast to following changes in the intensity of absorbance within a particular wavelength range, which is the way conventional fluorescent labels are used. The change measured by the present invention is a direct measure of the binding of the labeled second protein to the first protein.

This difference in polarization values of free labeled second protein vs. bound second protein:first protein complex is used to measure the bound and free ratios of the second protein and analyze its binding to the first protein when in the presence of a test substance. Such measurement may occur in either saturation or competition experiments. The FP assay of this invention can thus be used in many solutions, including in the cytoplasm of the cell.

The degree of polarization of the emission is measured without the necessity to separate the components in the mixture. Finally, the effect of the presence or concentration of the test substance is determined by comparing the ratio of the polarization levels of the mixture with the polarization levels of the same amounts of the first and second proteins/peptides in the absence of test compound.

If competitive binding occurs between the first or second protein and the test substance instead of between the two proteins, so that the protein:protein complex is not formed, the second protein will remain free in solution and low polarization will be measured. If the test substance is not an inhibitor or a good inhibitor, the complex will be formed and the polarization of the mixture will increase. Thus a decrease in the observed emission polarization depolarization values from known polarization levels of the first protein:second protein complex in the absence of test compound is noted in the presence of an inhibitor test substance.

Since the method of this invention follows changes in the ratio of polarization in the horizontal and vertical planes of the emission wavelength range, rather than changes in the intensity of absorbance within a particular wavelength range, the method is less vulnerable to interference from high absorbance of test compounds in solution.

The methods of this invention are susceptible to automation. For example, all or several of the steps outlined above may be performed by an apparatus programmed to conduct automatically two or more steps for a given test substance or one or more steps for a plurality of test substances or test substance concentrations. As one example, any standard fluorometer equipped for polarization experiments or measurements may be used in practicing this invention to both irradiate the mixture and measure the polarization. Wavelengths suitable to excite the fluorophore depend on the nature of the fluorophore, as described above. Typically, one uses cut off filters to define a wavelength range which is determined by the excitation and emission wavelengths of the fluorophore. For fluorescein carboxyamide peptides, one would typically use an excitation cutoff filter of 485 nM. Also, non-polarizing material should be used for any component of the apparatus, including the test chambers in which samples are evaluated, which will be in the light path. Plastics and fiber optics are generally avoided in such uses in favor of optical glasses, quartz, etc.

In addition to using standard fluorometers, one can also use specialty fluorometers such as the Jolley FPM1 (for individual samples) or the Jolley FPM2 (for high-throughput assays in 96-well format). Such fluorometers have been optimized for polarization measurements and have much higher sensitivity than standard fluorometers.

Other automated equipment may provide both the admixing step combined with the other steps, and/or the comparison of the polarization of the control mixture without the test substance and the test mixture with the test substance. One of skill in the area of automation may use various apparatus to substantially automate the assays of this invention.

In yet another aspect, the invention provides components or reagents, e.g., a protein bearing a covalently linked fluorophore, useful in the methods of the invention. The components or reagents can further be packaged in a kit with instructions for use in the described methods.

III. THE INHIBITORS

Once a compound has been identified as an inhibitor, it can be produced using known methods, such as by recombinant methods of protein production or chemical synthesis. It can also be obtained from the source in which it was initially identified.

A. Counterscreens

Having identified an inhibitor of a protein:ligand association by means of the assay of this invention, one may use counterscreens against one or more other protein:ligand pairs to identify nonspecific inhibitors, or confirm inhibitor specificity. Test compounds identified as inhibitors by the method of this invention may be further evaluated for binding activity with respect to one or more additional proteins of interest, or with respect to additional proteins containing the domain(s), using various approaches, a number of which are well known in the art. The counterscreen may be carried out using the methods and materials of the subject invention, or may be conducted using alternative approaches for the detection of direct or competitive binding, including, e.g., cell-based assays or surface plasmon resonance (BIAcore®) technology [see, e.g., Panayotou et al, *Mol. Cell. Biol.*, 13: 3567–3576 (1993)].

The inhibitors identified in the assay system of this invention can be further evaluated by conventional methods for assessing toxicological and pharmacological activity. For example, test compounds identified as inhibitors may further be evaluated for activity in inhibiting cellular or other biological events mediated by a pathway involving the protein:ligand interaction of interest using a suitable cell-based assay or an animal model. Cell-based assays and animal models suitable for evaluating inhibitory activity of a test compound with respect to a wide variety of cellular and other biological events are known in the art. New assays and models are regularly developed and reported in the scientific literature.

By way of nonlimiting example, compounds which bind to an SH2 domain involved in the transduction of a signal leading to asthma or allergic episodes may be evaluated in a mast cell or basophil degranulation assay. The inhibitory activity of a test compound identified as an SH2 inhibitor by the method of this invention with respect to cellular release of specific mediators such as histamine, leukotrienes, hormonal mediators and/or cytokines, as well as its biological activity with respect to the levels of phosphatidylinositol hydrolysis or tyrosine phosphorylation can be characterized with conventional in vitro assays as an indication of biological activity. [See, e.g., Edward L. Barsumian et al, *Eur. J. Immunol.*, 11:317–323 (1981); M. J. Forrest, *Biochem. Pharmacol.*, 42:1221–1228 (1991) (measuring N-acetyl-betaglucosaminadase from activated neutrophils); and V. M. Stephan et al., *J. Biol. Chem.*, 267:5434–5441 (1992)].

For example, histamine release can be measured by a radioimmunoassay using a kit available from AMAC Inc. (Westbrook, Me.). One can thus evaluate the biological activity of inhibitors identified by the method of this invention and compare them to one another and to known active compounds or clinically relevant compounds which can be used as positive controls.

Generally speaking, in such assays IC50 scores of 150–300 uM are considered of interest, scores of 50–150 uM arc considered good, and scores below about 50 uM are of high interest. Prior to or in addition to in vivo models, inhibitors identified by this invention may also be tested in an ex vivo assay for their ability to block antigen-stimulated contraction of sensitized guinea pig tracheal strip tissue. Activity in this assay has been shown to be useful in predicting the efficacy of potential anti-asthma drugs.

Numerous animal models of asthma have been developed and can be used [for reviews, see Larson, "Experimental Models of Reversible Airway Obstruction", in THE LUNG, Scientific Foundations, Crystal, West et al. (eds.), Raven Press, New York, pp. 953–965 (1991); Warner et al., *Am. Rev. Respir. Dis.*, 141:253–257 (1990)]. Species used in animal models of asthma include mice, rats, guinea pigs, rabbits, dogs, sheep and primates. Other in vivo models available are described in Cross et al., *Lab Invest.*, 63: 162–170 (1990); and Koh, et al., *Science*, 256:1210–1213 (1992).

By way of further example, inhibitors identified by the method of this invention which bind to a protein involved in the transduction of a signal involved in the initiation, maintenance or spread of cancerous growth may be evaluated in relevant conventional in vitro and in vivo assays. See e.g., Ishii et al., *J. Antibiot.*, XLII:1877–1878 (1989); and U.S. Pat. 5,206,249 (issued Apr. 27, 1993).

B. Uses of Inhibitors Identified by this Invention

Inhibitors identified by this invention may be used as biological reagents in assays as described herein for functional classification of a particular protein, particularly a newly discovered protein. Families or classes of proteins may thus be defined functionally, with respect to ligand specificity. Moreover, inhibitors identified by this invention can be used to inhibit the occurrence of biological events resulting from molecular interactions mediated by a the protein or protein:ligand pair of interest. Inhibiting such interactions can be useful in research aimed at better understanding the regulation and biological significance of such events.

Such inhibitory agents would be useful, for example, in the diagnosis, prevention or treatment of conditions or diseases resulting from a cellular process(es) mediated by a targeted interaction. For example, a patient can be treated to prevent the occurrence or progression of osteoporosis or to reverse its course by administering to the patient in need thereof an SH2 binding or blocking agent which selectively binds Src SH2.

There are many other conditions for which phosphopeptide binding or blocking agents may be useful therapeutically, including, e.g., breast cancer where the SH2 domain-containing proteins Src, PLCgamma and Grb7 have been implicated. Other relevant conditions include prostate cancer, in which case targeting Grb2, PLCg, and PI3K, all of which contain SH2 domains, may be useful in treatment or prevention of the disease. Inhibition of the interaction of Grb2 or Abl SH2 domains with Bcr-abl may be useful to treat chronic myelogenous leukemia (CML) or acute myelogenous leukemia (AML).

Still other relevant applications of a PBP inhibitor would be to prevent interferon-, growth factor-, or cytokine-mediated diseases (e.g. inflammatory diseases) by targeting the PBDs of STAT proteins. Agents that block the SH2 domains of ZAP-70, which is involved in activation of T-cells, would be useful in the treatment of autoimmune diseases. An inhibitor that blocks one or both SH2 domains of ZAP-70 would also be useful as an immunosuppressant to prevent rejection of skin and organ transplants.

Likewise, by further way of example, SH3 inhibtors would be useful in the diagnosis, prevention or treatment of conditions or diseases resulting from a cellular processes mediated by an SH3-based interaction. For example, a patient can be treated to prevent the occurence or progression of osteoporosis or to reverse its course by administering to the patient in need thereof an SH3 inhibitor which selectively binds to or inhibits interactions with src SH3. There are many other conditions for which SH3 inhibitors can be used therapeutically, including restenosis, rheumatoid arthritis, gout, asthma, emphysema, immune vasculitis, ulcerative colitis, psoriasis and acute respiratory distress syndrome, in which an SH3 of neutrophil oxidase p47 and p67 complex has been implicated. Other relevant conditions include chronic myelogenous leukemia, in which case SH3 domains of Grb-2 are targeted. It has recently been shown that the BCR-abl oncogene in CML participates in the ras pathway for growth stimulation through its interaction with Grb-2. In these cells, inhibition of the interaction of Grb-2

SH3 domains with the SOS oncogene will block its ability to stimulate cell proliferation. Still other relevant conditions include cancers such as breast cancer, glioblastomas, head and neck tumors and ovarian tumors, for which the SH3 domain of Grb-2 would be targeted. For example, tumors with associated amplification of receptors for EGF and PDGF could be inhibited by blocking activation of the Ras pathway through inhibition of the interaction between Grb-2 (SH3) and Ras. Furthermore, since the SH3 domain of Src family kinases are believed to be involved in activation of T-cells, B-cells, mast cells, and NK cells and since the SH3 domains of the tyrosine kinases Tsk and Btk are believed to be involved in T-cell (Tsk SH3) and B-cell (Btk SH3) function an SH3 inhibitor identified by the subject invention could be administered to a patient in need thereof to suppress immune function.

An inhibitor of a protein:ligand interaction identified by the method of this invention can be formulated into a pharmaceutical composition containing a pharmaceutically acceptable carrier and/or other excipient(s) using conventional materials and means. Such a composition can be administered to an animal, either human or non-human, for therapy of a disease or condition resulting from cellular events involving the targeted protein-ligand interaction. Administration of such composition may be by any conventional route (parenteral, oral, inhalation, and the like) using appropriate formulations as are well known in this art. The inhibitor can be employed in admixture with conventional excipients, ie, pharmaceutically acceptable organic or inorganic carrier substances suitable for parenteral administration.

C. Pharmaceutical Compositions and Methods i. Compositions

Inhibitors identified by this invention can be formulated into pharmaceutical compositions containing a therapeutically (or prophylactically) effective amount of the inhibitor in admixture with a pharmaceutically acceptable carrier and/or other excipients (i.e., pharmaceutically acceptable organic or inorganic carrier substances suitable for parenteral administration) using conventional materials and means. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Topical compositions include a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils. Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary.

Materials and methods for producing the various formulations are well known in the art [see e.g. U.S. Pat. Nos. 5,182,293 and 4,837,311].

ii. Methods

The invention provides methods of treating, preventing and/or alleviating the symptoms and/or severity of a disease or disorder referred to above by administration to a subject of the inhibitor in an amount effective therefor. The subject will be an animal, including but not limited to animals such as cows, pigs, chickens, etc., and is preferably a mammal, and most preferably human. By "mammals" is meant rodents such as mice, rats and guinea pigs as well as dogs, cats, horses, cattle, sheep, nonhuman primates and humans. Such effective amounts can be readily determined by evaluating the inhibitors identified by this invention in conventional assays well-known in the art, including assays described herein.

Administration of such composition may be by any conventional route using appropriate formulations as are well known in this art. Various delivery systems are known and can be used to administer the inhibitor, e.g., encapsulation in liposomes, microparticles, microcapsules. One mode of delivery of interest is via pulmonary administration. Other methods of introduction include but are not limited to intradermal, intramuscular, intraperitoneal, intravenous, subcutaneous, intranasal, epidural, nasal and oral routes. The inhibitor may be administered by infusion or bolus injection, by absorption through epithelial or mucocutaneous linings (e.g., oral mucosa, rectal and intestinal mucosa, etc.) and may be administered together with other biologically active agents.

Administration can be systemic or local. For treatment or prophylaxis of nasal, bronchial or pulmonary conditions, preferred routes of administration are oral, nasal or via a bronchial aerosol or nebulizer. In specific embodiments, it may thus be desirable to administer the inhibitor locally to the area in need of treatment; this may be achieved by, for example, and not by way of limitation, local infusion during surgery, topical application, by injection, by means of a catheter, by means of a suppository, or by means of a skin patch or implant, said implant being of a porous, nonporous, or gelatinous material, including membranes, such as sialastic membranes, or fibers.

Administration to an individual of an effective amount of the inhibitor can also be accomplished topically by administering the compound(s) directly to the affected area of the skin of the individual. In certain instances, it is expected that the inhibitor may be disposed within devices placed upon, in, or under the skin. Such devices include patches, implants, and injections which release the compound into the skin, by either passive or active release mechanisms.

The amount of the inhibitor which will be effective in the treatment or prevention of a particular disorder or condition will depend on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. For example, a typical effective dose of the inhibitor is in the range of about 0.01 to about 50 mg/kgs, preferably about 0.1 to about 10 mg/kg of mammalian body weight, administered in single or multiple doses. Generally, the inhibitor may be administered to patients in need of such treatment in a daily dose range of about 1 to about 2000 mg per patient.

The precise dosage level of the inhibitor, as the active component(s), should be determined by the attending physician or other health care provider and will depend upon well known factors, including the phosphopeptide binding interaction under consideration, the route of administration, and the age, body weight, sex and general health of the individual; the nature, severity and clinical stage of the disease; and the use (or not) of concomitant therapies.

C. Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

Other components such as physiologically acceptable surfactants (e.g., glycerides), excipients (e.g., lactose), carriers, and diluents may also be included.

The following examples illustrate various aspects of this invention. These examples do not limit the scope of this invention which is defined by the appended claims. The contents of all references, pending patent applications, published patent applications, issued patents and information contained in web sites, cited throughout this application (including the "Background" Section) are hereby expressly incorporated by reference.

IV. EXAMPLES

The following examples illustrate various aspects of this invention. These examples do not limit the scope of this invention which is defined by the appended claims.

The introduction of a 96-well plate reader (FPM2, Jolley Instruments) with a high sensitivity towards fluorescein and fluorescein conjugates (in the low nanomolar probe concentration range) has allowed the development of 96-well based FP assays. These examples describe an FP assay and the necessary components for measuring the binding of compounds to the Src-SH2 domain.

Example 1

PEPTIDE SYNTHESIS

Peptide synthesis was performed manually using Fmoc-Rink amide resin [4-(2',4'-dimethoxyphenyl-Fmoc-aminomethyl) phenoxy resin; (Advanced Chemtech)] with substitution levels of 0.3–0.6 mmole/g. Standard FMOC synthesis methods were used. The wash and deprotection solvent used was dimethyl acetamide (DMA); the coupling solvent used was N-methylpyrrolidone (NMP). For amino acid couplings, four equivalents of amino acid, four equivalents of coupling reagent, 2-(1H-benzotriazole-1-yl)-1,1,3,3-tetramethyluronium tetrafluoroborate (TBTU), and eight equivalents of N-methylmorpholine (NMM) were used per equivalent of amine on the resin. Amino acids used were Fmoc-Gly, Fmoc-Glu(Tbu), Fmoc-Ile, Fmoc-Thr(Tbu), and Fmoc-Tyr(Tbu). Fmoc deprotection was done using 20% piperidine in DMA.

Peptides were phosphorylated on the solid-phase using standard methodology [see, e.g., Merrifield, *J. Am. Chem. Soc.*, 85:2149–2154 (1963)]. Resins and 1-1,H-tetrazol were dried under vacuum over $P_2O_5$ overnight. To a portion of resin (0.1–0.5 g) mixed with 50 equivalents of 1-1,H-tetrazole was added 1 ml/0.1 g of dry DMA. The resin was stirred and swelled for 20 minutes. 10 equivalents of dibenzyl N,N-diethylphosphoramidite (Toronto Research Chemicals, Inc.) was then added, the resin mixture was stirred for 15 minutes, sonicated for 30 minutes, and stirred for 15 minutes. Resin was washed 5× with DMA. Oxidization was performed by adding 3 equivalents of chlorobenzylperoxide in DMA, with stirring for 30 minutes, and sonication for 30 minutes. Finally, peptides were washed 5× DMA, 3× $CH_2Cl_2$, and 3× MeOH, followed by vacuum drying overnight.

Final cleavage from the resin and side chain deprotection was done using 90:10:10:5 ratios of trifluoroacetic acid (TFA):$H_2O$:ethane dithiol (EDT):tri-isopropyl silane (TIPS). Scavengers were added to resin, followed by addition of TFA with stirring for 2.5 hours. Resin was filtered off. TFA was removed by blowing under $N_2$ for several hours. Crude peptide slurry was resuspended in water, and extracted three times with an equal portion of ice-cold diethyl ether. Excess ether was removed by blowing under $N_2$. The crude peptide mix was lyophilized overnight.

All peptides were purified in the following manner. Crude lyophilized peptides were dissolved in DMSO at a concentration of 100–300 mgs per ml. Peptides were purified on a Semi-Preparative reverse phase HPLC column (Vydac). A series of 15–30 ul injections of crude peptides in 100% DMSO were used. Purity was checked using an analytical reverse phase HPLC column, with a diode-array spectrophotometer. One pass was adequate to give greater than 90% purity.

Example 2

PROBE SYNTHESIS

Figure 1:
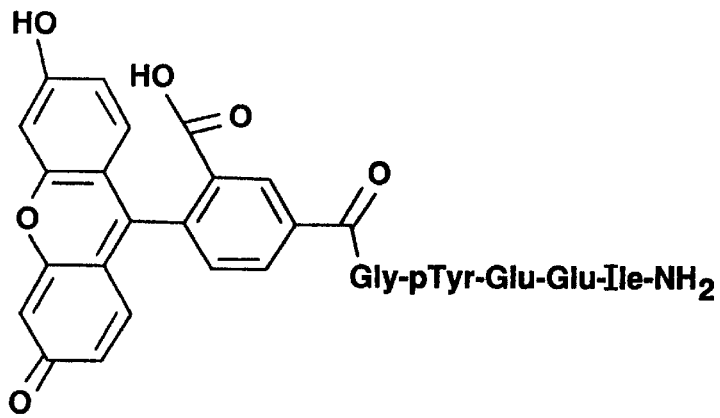
FIG. 1 depicts the structure of a fluorescent probe FMT1, described in Example 2.
Figure 5:
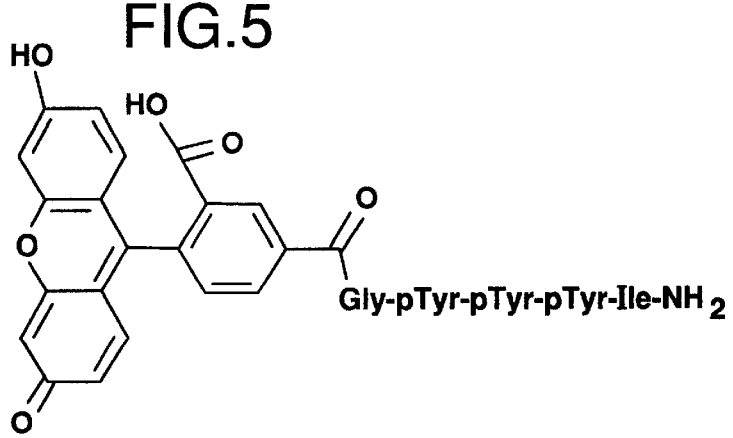
FIG. 5 depicts the structure of an alternative fluorescent probe for use in the Src-SH2 assay, described in Example 2.

An exemplary fluorescent probe (FIG. 1 or FIG. 5) was designed to consist of the fluorescent moiety, 5-carboxyfluorescein, coupled to a pentapeptide ligand based on the known Src-SH2 high affinity tetrapeptide sequence derived from the core middle-T antigen. The peptide ligand sequence is GpYEEI, containing the core middle-T antigen high-affinity Src-SH2 sequence (pYEEI), with an N-terminal glycine for ease of coupling.

5-Carboxyfluorescein was chosen for several reasons. It is one of the few defined isomer fluoresceins available. It yields a conjugate with less flexibility than many available fluoresceins, which is important for minimizing the "propeller effect" that can interfere with FP based measurements and an activated version is commercially available (Molecular Probes, Inc.).

The probe sequence was prepared as follows: The peptide GpYEEI was coupled to the fluorescein moiety directly on the resin. The peptide sequence was assembled on Rink amide resin, and phosphorylated as described above. The resultant sequence was Fmoc-GpYEEI-RINK. The peptide/resin was deprotected with 20% piperidine in DMA, removing the FMOC protecting group, and leaving the free-amino terminus available for coupling. After thorough washing with DMA, 1.1 equivalent of 5-carboxyfluorescein succinimidyl ester (Molecular Probes) was added with 6 equivalents of diisopropylethylamine. Coupling was carried out for 1.5 hours, followed by 1 NMP and 3 DMA washes, and by a repeat coupling as above. The completed probe was cleaved and worked up as described above, yielding a probe termed FMT1.

Two exemplary labeled probes for Src SH2 domain, prepared as described above are:

fluorescein-G-pYEEI-NH$_2$ and
fluorescein-pYpYpYIE-NH$_2$.

Example 3

PROTEIN PRODUCTION—Src

Human Src encoding residues 145–251 [Tanaka, A. and Fujita, D. J., *Mol. Cell. Biol.* 6:3900–3909 (1986)] was cloned into the pT7 expression vector and transformed into *E. coli* BL21 (DE3). Protein was produced from the growth and induction of 27 liters of culture in minimal medium. In a typical preparation, the culture was grown at 37° C. to an optical density (OD) of 1.0 at 595 nm. The culture was induced with 1 mM isopropyl—D-thiogalactopyranoside (IPTG) and the temperature was dropped to 25° C. The culture was harvested 21 hours later.

The cells were lysed in 50 mM potassium phosphate, 250 mM NaCl, 5 mM DTT, 2 mM EDTA, 1 mm PMSF, pH 7.0 using a French pressure cell at 16,000 psi. The protein was purified over carboxy-sulfon (J. T. Baker), a weak-strong cation exchanger. The column was equilibrated with 50 mM potassium phosphate, 5 mM DTT, 0.02% NaN$_3$, pH 7.0 and loaded with filtered bacterial lysate at 2 ml/minute. The Src protein was eluted with a 1 M NaCl gradient. The eluate was concentrated using a Centriprep 10 concentrator (Amicon, 10,000 MW cutoff) and centrifuged at 3000 ×g. The protein was then purified by gel filtration on a Sephacryl S-100 (Pharmacia) column equilibrated with 20 mM potassium phosphate, 50 mM NaCl, 5 mM DTT, 1 mM EDTA, 0.02% NaN$_3$, pH 7.4. Purity, as measured by SDS gel electrophoresis and RP-HPLC, is >95%. The purified protein is stored frozen in 50 mM potassium phosphate, 500 mM NaCl, 10% glycerol, 5 mM DTT, 5 mM EDTA, 0.02% NaN$_3$, pH 7.4.

Example 4

A FLUORESCENCE-POLARIZATION BASED SRC-SH2 BINDING ASSAY

A. FP—General

All polarization methods were performed on an FPM2 96-well plate reader (Jolley), with standard cutoff filters (excitation=485 nm; emission=530 nm). Saturation experiments were used to explore various conditions for the assay, with the aim of maximizing the protein and assay stability, and of determining $K_d$s of the protein/probe interaction.

B. Saturation Experiments

For saturation experiments, fixed concentrations of probe were used, and increasing concentrations of Src-SH2 were added. This is the reverse of the way such assays are commonly done with radioactive ligands.

A saturation experiment was conducted in which the Src-SH2 domain is varied in concentration from a high of 40 uM to a low of 39 nM. The fluorescent probe FMT1 (FIG. 1) was kept at a fixed concentration of 20 nM. Amino acid analysis was used to quantitate both the protein and probe concentrations. The results are illustrated in the saturation curve and Scatchard analysis of FIGS. 2A and 2B, respectively from this experiment.

Figure 2A:
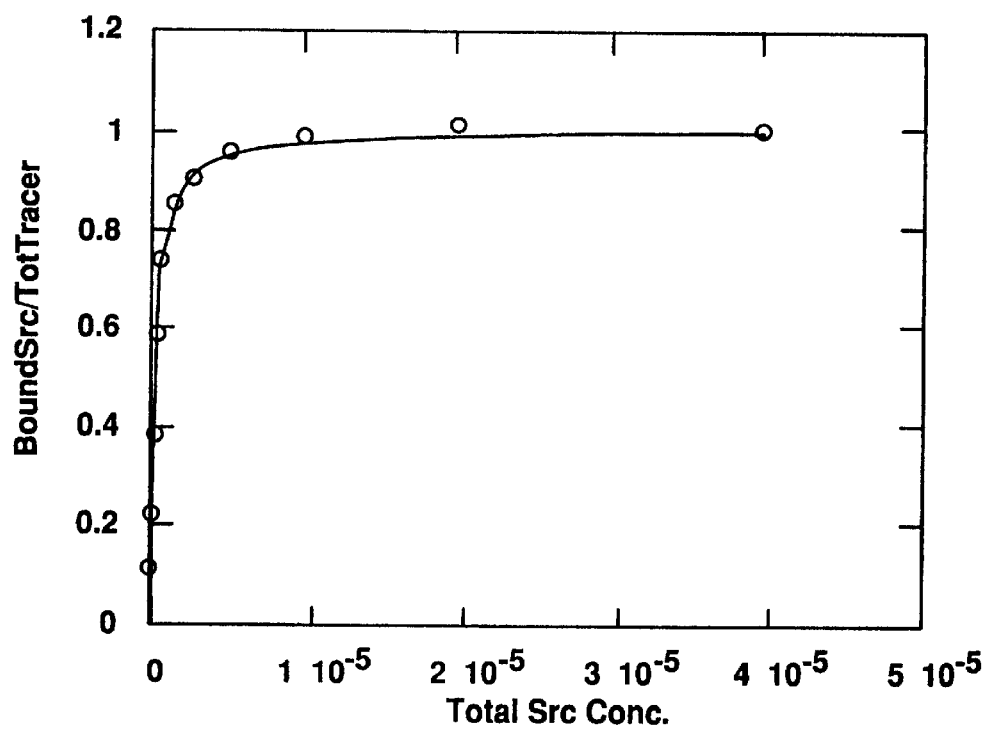
FIG. 2A is the saturation curve of FMT1 binding to Src SH2, which plots bound Src/total tracer vs. total Src concentration. Non-linear least squares fit for a saturation experiment between probe FMT1 and the Src-SH2 domain. Calculated Kd is 0.24 with an error of 0.008 M, (Chi)$^2$ of 0.0027, R of 0.9987.
Figure 2B:
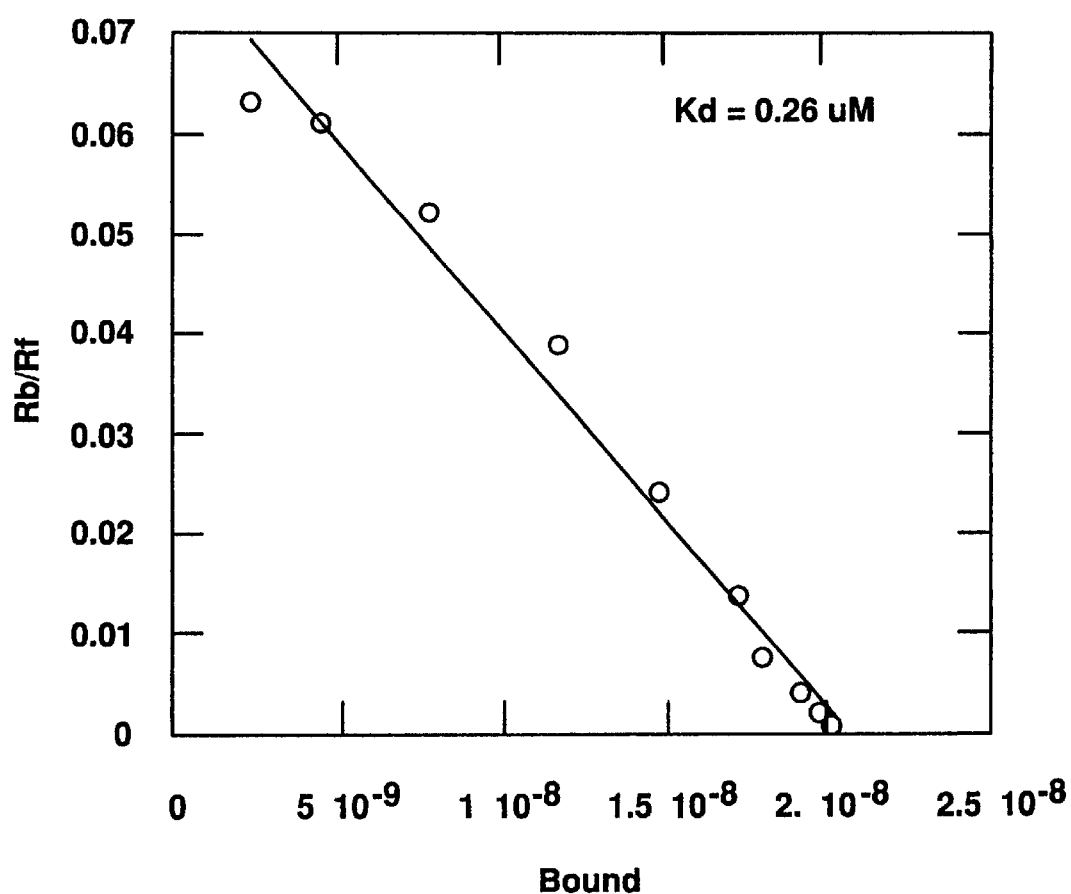
FIG. 2B is the Scatchard analysis (transformation) of the data in FIG. 2A, plotting Rb/Rf vs. Bound. Calculated Kd is 0.26 M, with an R value of 0.992 for the linear fit.

The data shown in FIGS. 2A and 2B show that the affinity of the probe for the receptor domain is appropriate for conducting competitive binding assays and that saturable binding to a single site is observed, consistent with the assay of this invention and with competitive, reversible binding to a single site.

C. Competition Experiments

For competition experiments, fixed concentrations of probe and protein were used, and increasing concentrations of peptides were added.

The designed probe FMT-1 has a Kd of ~0.3 uM towards Src-SH2 in the standard buffer conditions. Some variation in observed Kd values will occur with changes in buffer conditions.

Figure 3:
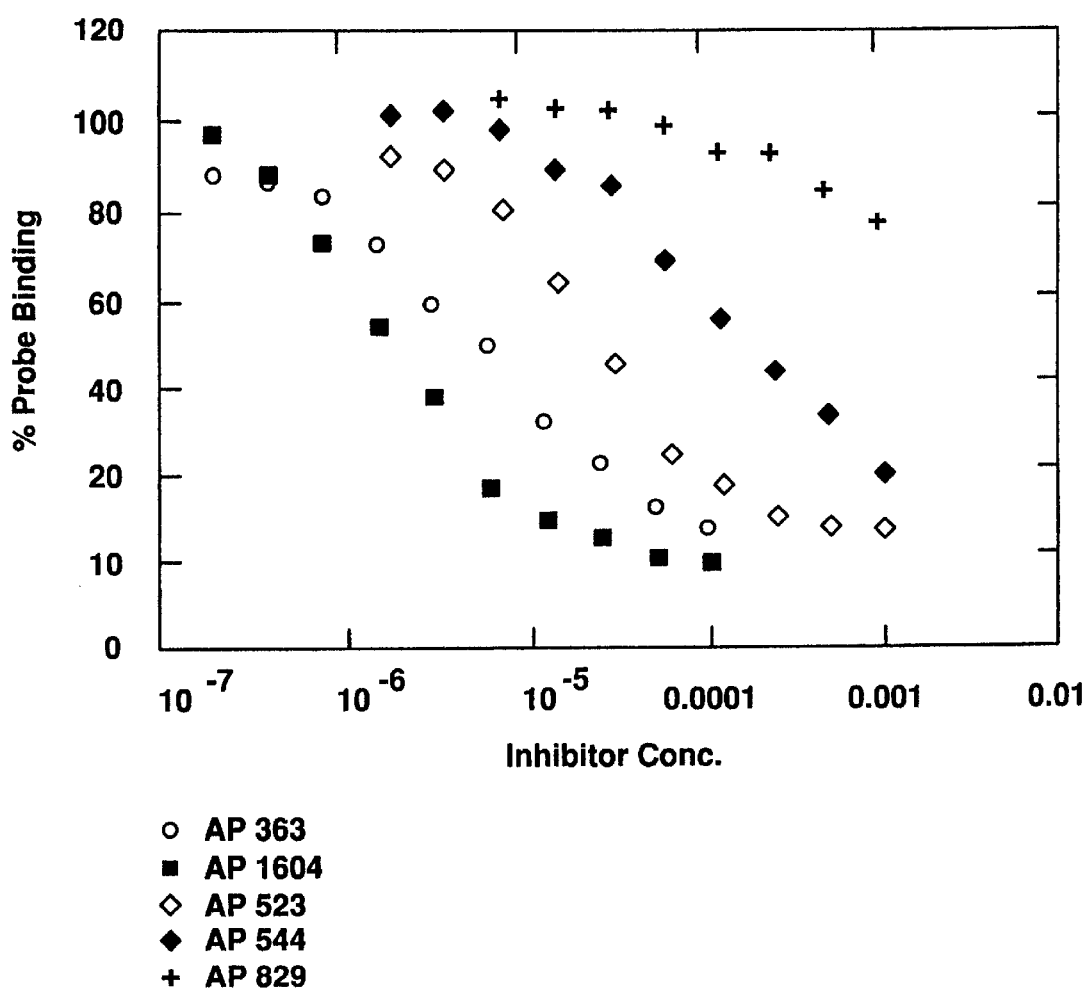
FIG. 3 is an Src competition curve (2% DMSO) plotting % probe binding vs. inhibitor concentration for the following tetrapeptides: Ac-pYEEI (open circle); Ac-pYpYEEI (closed square); Ac-pYGGL (plus sign); Ac-pYEDL (open triangle); Ac-DGVpYTGL (closed triangle).
Figure 4A:
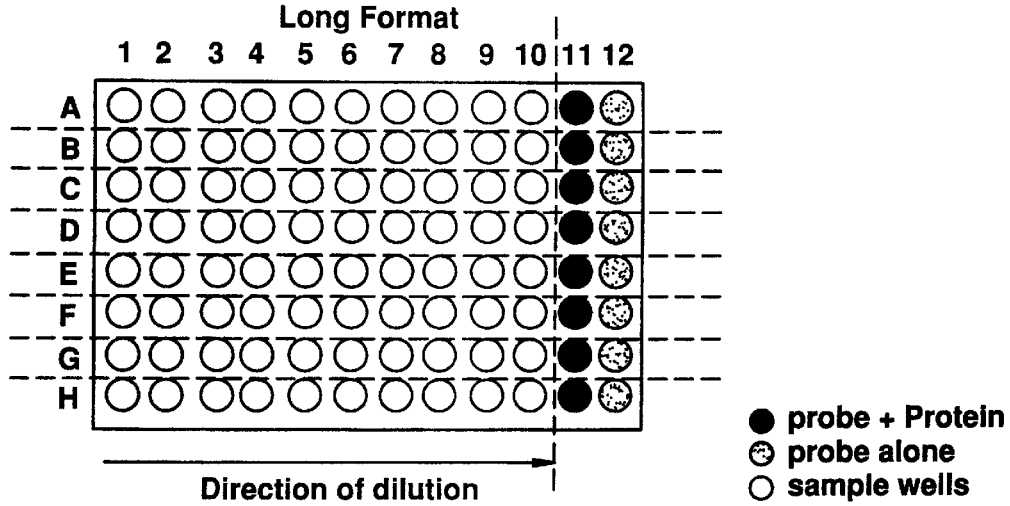
FIG. 4A is a depiction of a 96 well plate of the experiment of Example 5, long format, with an arrow illustrating the direction of dilution. Clear circles are sample wells, gray circles are wells containing probe alone and dark circles are wells containing probe and protein.
Figure 4B:
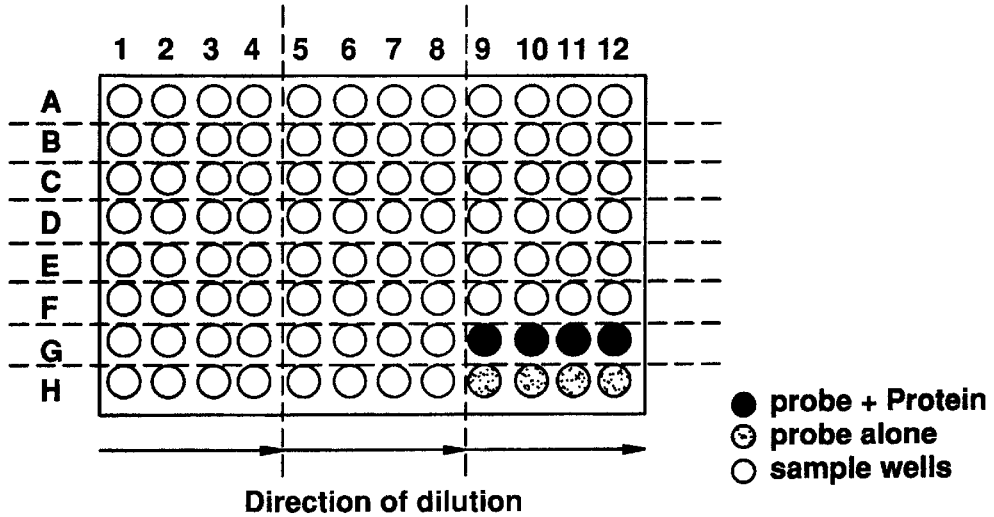
FIG. 4B is a depiction of a 96 well plate of the experiment of Example 5, short format, with an arrow illustrating the direction of dilution per 4 rows of wells. Circles are defined as in FIG. 4A.

As illustrated in FIG. 3, a Src competition assay (2% DMSO buffer) was conducted for the following tetrapeptides: Ac-pYEEI (open circle); Ac-pYpYEEI (closed square); Ac-pYGGL (plus sign); Ac-pYEDL (open triangle); Ac-DGVpYTGL (closed triangle). FIG. 3 shows the competition curve plotting % probe binding vs. inhibitor concentration obtained in one set of experiments.

TABLE 1

Representative Peptide competitive IC50s

| Sequences | Number | IC$_{50}$ |
| --- | --- | --- |
| Ac-pYEEI | 1 | 8 |
| Ac-pYpYEEI | 2 | 1.5 |
| Ac-pYpYpYIE | 3 | 0.5 |
| Ac-pYTGL | 4 | 100 |
| Ac-pYGGL | 5 | 700 |

Data of this sort demonstrates that the materials and methods of this invention can be used to conduct a competitive binding assay with inhibitory substances having a range of IC$_{50}$ values.

Illustrative protocols according to this invention are both manual and automated and are performed as follows:

D. Manual Assays

Two different plates can be run for each experiment—a 2% DMSO and 20% DMSO plate.

Buffers

All buffer components were low-fluorescence grade (Panvera Corporation). Standard (STD) buffer contains 20 mM phosphate (pH 7.4), 100 mM NaCl, 2 mM DTT, 1 mM EDTA, and 100 ug/ml BGG. Standard buffer is prepared by preparing NaCl, EDTA and phosphate stocks in Millipore water or the cleanest available water supply. The buffer is brought to volume in the same clean water.

The five buffers needed for these experiments are standard (STD) buffer, STD Buffer +4% DMSO, 100% DMSO, STD buffer with labelled probe alone and STD buffer with Src protein and labelled probe.

One liter is made up of 100 ml of 1M NaCl, 20 ml of 1M phosphate (pH 7.4), 2 ml of 500 mM EDTA, 20 ml of 5 mg/ml BGG, and 858 ml of Clean Water.

The standard buffer is made up and stored at 4° C. Before each use, the DTT is added at 2 mM. This standard buffer is employed to make up the Standard Buffer +4% DMSO stock also. This can be stored at 4° C. as well and DTT can be added before use.

Protein and Control Peptide

The SRC protein is used at a concentration of 0.75 uM final. An example of SRC stock solution is 416.6 uM in STD buffer. The peptide Ac-pYEEI is used at 100 uM final. It is desirable to make a 2x stock of this. For assays where the tighter-binding pYpYpYIE probe is used, the Src protein concentration can be reduced to 150 nM. In general, the concentration of the protein can be adjusted to match the affinity of the probe.

Probe

Fluor-GpYEEI is used as the probe at a concentration of 20 nM final. The probe stock sent is 10 uM in STD buffer.

As one example, to prepare 25 mls of protein and only 2 mls of probe alone, the following steps are followed:

(a) 27 mls Standard buffer (add 2 mM DTT)
(b) Add Probe-1515 at 2x or 40 nM=108 uL
(c) Remove 2 mls for Probe Alone
(d) To the remaining 25 mls add SRC at 2x or 1.50 uM=90 uL This is now the Protein and Probe solution.

Secondary Stocks

Each compound/peptide and the control peptide is in separate tubes. They are at 2x stocks.

It is desirable to make primary stock at 50 mM in 100% DMSO, then make the secondary stocks in STD Buffer+4% DMSO at the appropriate concentration for the desired experiment.

One example of a secondary stock is made by combining 2 mM stock in STD Buffer+4% DMSO for one embodiment of an assay (Long Format, 2% DMSO). Another is 5 mM stock in 100% DMSO for Long Format assay with 20% DMSO. Another secondary stock solution is 400 uM stock in STD buffer+4% DMSO for Short Format assay #1 and #2 —2% DMSO. 1 mM stock in 100% DMSO for Short Format #1 and #2 —20% DMSO Long Format Assay A 1:2 dilution is used with first well at 1 mM final. For Plate 1—2% DMSO, the assay protocol is as follows:

(a) 50 ul Standard Buffer+4% DMSO in column 2-12.
(b) 100 ul of 8 different compounds (2 mM stock/SB+4% DMSO) in each well in column 1 row A–H.
(c) Serially dilute 50 ul (1:2) horizontally down plate to column 10.
(d) Add 50 ul probe alone to column 12.
(e) Add 50 ul protein and probe to column 1-11.
(f) 100 ul final volume per well.
(g) Read plate on FPM2.

For Plate 1–20% DMSO, the assay protocol is as follows:

(a) 20 ul 100% DMSO in columns 2–12.
(b) 40 ul of 8 different compounds (5 mM stock/100% DMSO) in each well in column 1 row A–H.
(c) Serially dilute 20 ul (1:2) horizontally down plate to column 10.
(d) Add 50 ul probe alone to column 12.
(e) Add 50 ul protein and probe to column 1-11.
(f) Add 50 ul STD buffer to entire plate.
(g) 100 ul final volume per well.
(h) Read plate on FPM2.

Short Format #1 Assay

A 1:3 dilution with first well at 200 uM final. Compounds/peptides are used in duplicate. These examples are for a 1:3 dilution but volumes may be changed to accommodate any desired dilution.

For Plate 1–2% DMSO, the assay protocol is as follows:

(a) 50 ul Standard Buffer+4% DMSO in row B–D and F–G.
(b) 75 ul of 11 different compounds (400 uM/SB+4% DMSO) in duplicate each well in column 1-10, row A and column 1-12, row E.
(c) Serially dilute 25 ul (1:3) vertically down plate from A–D then from E–H.
(d) Add 50 ul probe alone to column 12.
(e) Add 50 ul protein and probe to column 1-11 A–D and 1-12 E–H.
(f) 100 ul final volume per well.
(g) Read plate on FPM2.

For Plate 2–20% DMSO, the assay protocol is as follows:

(a) 20 ul 100% DMSO in row B–D and F–G.
(b) 30 ul of 11 different compounds (1 mM/100% DMSO) in duplicate each well in column 1–10, row A and column 1–12, row E.
(c) Serially dilute 10 ul (1:3) vertically down plate from A–D then from E–H.
(d) Add 50 ul probe alone to column 12.
(e) Add 50 ul protein and probe to column 1–11 A–D and 1–12 E–H.
(f) 100 ul final volume per well.
(g) Add 30 ul STD buffer to entire plate.
(h) Read plate on FPM2.

Short Format #2 Assay

A 1:3 dilution with first well at 200 uM final. Compounds/peptides are used in singly. These examples are for a 1:3 dilution but volumes may be changed to accommodate whatever dilution you wish.

For Plate 1–2% DMSO, the assay protocol is as follows:

(a) 50 ul Standard Buffer+4% DMSO in column 2–4 and 6–8 in 10–12.
(b) 75 ul of 16 different compounds in (400 uM/SB+4% DMSO) each well in column 1 and 5.
(c) 75 ul of 6 different (400 uM/SB+4% DMSO) compounds to column 9, A–F only. Total of 22 compounds.
(d) Serially dilute 25 ul (1:3) horizontally down plate from 1–4 then from 5–8, then from 9–12.
(e) Add 50 ul probe alone to row H, columns 9–12.
(f) Add 50 ul protein and probe row A–H, columns 1–8 and A–G, columns 9–12.
(g) There should be 100 ul final volume per well.
(h) Read plate on FPM2.

For Plate 2–20% DMSO assay, the following protocol is followed:

(a) 20 ul 100% DMSO in column 2–4 and 6–8 and 10–12.
(b) 30 ul of 16 different compounds (1 mM/100% DMSO) in each well in column 1 and 5.
(c) 30 ul of 6 different compounds (1 mM/100% DMSO) to column 9, A–F only. Total of 22 compounds.
(d) Serially dilute 10 ul (1:3) horizontally down plate from 1–4 then from 5–8, then from 9–12.
(e) Add 50 ul probe alone to row H, column 9–12.
(f) Add 50 ul protein and probe row A–H, columns 1–8 and A–G, columns 9–12.
(h) Add 50 ul STD buffer to entire plate.
(i) There should be 100 ul final volume per well.
(j) Read plate on FPM2.

E. Automated Assays
  (1) Short dilution
  This assay is run with ⅓ dilution steps with first well at 200 uM, 4 wells down, 22 cpds/plate, "landscape" orientation of plate with respect to Genesis deck.
    (i) 20% DMSO
    (ii) 2% DMSO
  (2) Long dilution
  This assay is run with ½ dilution steps with first well at 1 mM, 10 wells down, 8 cpds/plate, "landscape" orientation of plate with respect to Genesis deck.
    (i) 20% DMSO
    (ii) 2% DMSO
  Dilution
  5 Buffers:
  Buffer+4% DMSO
  100% DMSO
  Buffer with probe alone
  Buffer with protein and probe
  Buffer
  (3) Short Format
  Each compound is in a separate well of a 96 well plate.
  Plate 1–2% DMSO
  50 ul 4% DMSO in columns 2, 3, 4, 6, 7, 8, 10, 11 and 12.
  75 ul of 22 different compounds (400 uM stock, 4% DMSO) each well in all rows of columns 1 and 5 and rows A through F of column 9.
  75 ul of Buffer+4% DMSO to wells G9 and H9.
  Serially dilute 25 ul (1:3) across plate from 1 to 4, throwing away last 25 ul, then from 5 to 8, and 9 to 12. This leaves 50 ul of liquid/well.
  Add 50 ul protein and probe to the entire plate except wells H9, 10, 11 and 12.
  Add 50 ul probe alone to wells H9, 10, 11 and 12.
  100 ul final volume per well.
  Read plate.
  Plate 2–20-% DMSO
  20 ul 100% DMSO in columns 2, 3, 4, 6, 7, 8, 10, 11 and 12.
  30 ul of 22 different compounds (1 mM stock, 100% DMSO) each well in all rows of columns 1 and 5 and rows A through F of column 9.
  30 ul of 100% DMSO to wells G9 and H9.
  Serially dilute 10 ul (1:3) across plate from 1 to 4, throwing away last 25 ul, then from 5 to 8, and 9 to 12. This leaves 50 ul of liquid/well.
  Add 50 ul protein and probe to the entire plate except wells H9, 10, 11 and 12.
  Add 50 ul probe alone to wells H9, 10, 11 and 12.
  Add 30 ul STD buffer to entire plate.
  100 ul final volume per well.
  Read plate.
  (4) Long Format
  Each compound is located in a separate well of a 96 well plate.
  Plate 1–2% DMSO
  50 ul 4% DMSO in columns 2–12.
  100 ul of 8 different compounds in each well in column 1, row A–H.
  Add 50 ul of std. 3 to well A11.
  Serially dilute 50 ul (1:2) across plate to column 10, throwing away last 50 ul (all rows).
  Serially dilute 50 ul from well A11 down to H11, throwing away last 50 ul.
  Add 50 ul protein and probe to the entire plate except A12, B12, C12 and D12.
  Add 50 ul probe alone to A12, B12, C12 and D12.
  100 ul final volume per well.
  Read plate.
  Plate 2–20-% DMSO
  20 ul 100% DMSO in rows 2–12.
  40 ul of 8 different compounds in each well in column 1, row A–H.
  Add 20 ul of std. 4 to well A11.
  Serially dilute 20 ul (1:2) across plate to column 10 throwing away last 20 ul (all rows).
  Serially dilute 20 ul from well A11 down to H11, throwing away last 20 ul.
  Add 50 ul protein and probe to the entire plate except A12, B12, C12 and D12.
  Add 50 ul probe alone to A12, B12, C12 and D12.
  Add 30 ul STD buffer to entire plate.
  100 ul final volume per well.
  Read plate.
* Once diluted, the plate can be read between 5 and 30 minutes.
* Assay plate is transferred to FPM2 machine for 3 minute read.

Example 5

FP-BASED ZAP, SYK, and LCK ASSAYS

In addition to the example of the Src SH2 domain and its phosphoTyr-containing peptide ligand which is linked to the fluorophore which are exemplified in Examples 1–4 above, the assay has also been used for the proteins Zap, Syk and Lck. Those three proteins are produced analogously to the production of Src in E. Coli, as described above with slight variations in production parameters such as salt concentration, DTT concentration, protein concentration, temperature and the like. While Src has a single SH2 domain, ZAP and Syk comprise two SH2 domains and the Lck protein comprises one SH2 domain and one SH3 domain.

The "first proteins" produced for these assays are produced generally as described for Src aa145–251 in Example 3. The proteins are represented in the table below. The term "NC" means that the first protein contains both the N terminal and C terminal SH2 domains. The sequences of Zap, Syk and Lck are known in the art. See also PCT/US96/13918

TABLE I

| First Protein | Amino Acid Residues of the Naturally Occurring Protein |
|---|---|
| NC-ZAP | aa1-259 |
| NC-Syk | aa1-260 |
| Lck | aa 109-266 |

The probes for each assay are designed and used as described above. For example, an exemplary probe for N,C-ZAP proteins, i.e., proteins containing the two SH2 domains of human ZAP in series, is fluorescein-GpYNELNLGRRGEEpYEVL-NH$_2$. As another example, an exemplary probe for N,C-Syk proteins, i.e., proteins containing the two SH2 domains of human Syk in series, is fluorescein-ApYTGLSTRNQETpYETL-NH$_2$. The SRC probe was also used with Lck.

The Lck protein has been assayed against fluorophore-labeled phosphopeptide ligand for the SH2 domain, fluorophore-labeled peptide ligand for the SH3 domain and fluorophore-labeled phosphopeptide double ligand for the SH2 and SH3 domains.

The assay format described in Example 4 is reproduced for these binding pairs and results obtained.

The data shown in FIGS. 2A and 2B show that the affinity of the probe for the receptor domain is appropriate for conducting competitive binding assays and that saturable binding to a single site is observed, consistent with the assay of this invention and with competitive, reversible binding to a single site. The data obtained from the saturation assay can, within the methods of the present invention, be used to assess whether a particular probe would be useful. For example, if a probe performs at a particular level in a saturation assay (e.g., Kd<10 uM and mP difference values>50 (difference in observed polarization in the presence and absence of protein)), it is indicative of its suitability for use in a competition assay of this invention.

Example 6

A FLUORESCENCE-POLARIZATION BASED HUMAN GRB2-SH2 AND YES-SH2 BINDING ASSAYS

A. Assay—General

GRB2 is a signal transduction protein containing two SH3 domains and one SH2 domain. The selectivity of the GRB2 SH2 domain for SH2 peptides is different from that of Src SH2, and thus it can be used as a counter screen for Src. The SH2 binding preference for GRB2 SH2 is pYXNX (Asn at the +2 position).

All assay methods, including buffers and instrumental usage, were performed generally as in the case of Src SH2 assay described in the previous examples, but substituting a human GRB2 protein (for Src SH2) and a probe specific for the GRB2 SH2 domain (in place of the Src-specific probe). The human GRB2 protein tested in the assay comprised amino acid residues 55–152 of huGRB2 [see Cell 70: 431–442 (1992)], although longer sequences encompassing the SH2 domain may also be used. Production and purification of the protein domain was similar to methods described above, especially the use of a phosphotyrosine column to purify the GRB2 SH2domain.

Additional counter screening can be performed with the Yes SH2 domain, which has a high degree of homology to Src and therefore can be used to screen compounds for specificity toward Src. Due to the high homology of these two proteins, standard probes for the Src SH2 domain are used in these assays.

B. Saturation Experiments

As in previous examples, saturation experiments were performed with fixed concentrations of probe and increasing concentrations of Grb-2-SH2.

The following Grb-2-specific SH2 probe ("FPgb2") was synthesized using the techniques described in Example 1

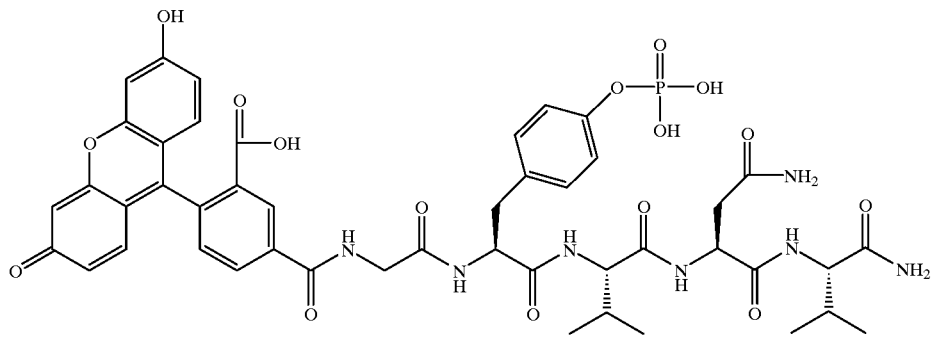

FPgb2, Fluor-GpYVNV-NH2 in which "Fluor" represents 5-carboxyfluorescein conjugated through an amide bond to the peptide containing the sequence GpYVNV. That tetrapeptide sequence is specific for Grb-2 SH2 domain binding. This probe had appropriate characteristics and an appropriate saturation curve with the GRB2 SH2 protein to (e.g., appropriate Kd and total mP difference on protein binding) to serve as a probe for a competition assay.

Example 7

A FLUORESCENCE-POLARIZATION BASED Src SH3 BINDING ASSAY

A. Assay—General

All assay methods, including buffers and instrumental usage, were performed generally as in the case of Src SH2 assay described in a previous example(s), but substituting a protein containing peptide sequence spanning the Src SH2 and SH3 domains (amino acid residues 84–251) [see Mol. Cell. Biol. 7(5): 1978–1983 (1987)], and a probe specific for the Src SH3 domain (in place of the Src-specific SH2 probe). Note that larger or smaller Src proteins may be used, so long as they include the Src SH3 domain (with or without the Src SH2 domain). Production and purification of the protein were essentially as described above, e.g., see Example 3. The following details are provided:

Src-SH2-SH3 Domain Purification:
1) French press lysis, 50 mM Potassium phosphate, 5 mM DTT, 2 mM EDTA, 1 mM PMSF, pH 7.0
2) 40 um WP Carboxy-sulfon column→633 mgs
3) Phosphotyrosine Agarose column→512 mgs
4) Dialysis against 50 mM Potassium phosphate, 10% Glycerol, 500 mM NaCl, 5 mM EDTA, 0.02% NaN3, pH 7.0

B. Saturation Experiments

As in a previous example(s), saturation experiments were performed with fixed concentrations of probe and increasing concentrations of Src-SH2-SH3 protein.

The following Src SH3 specific probe ("FPSH3") was synthesized using the techniques described in Example 1:

Fluor-PLARRPLPPLP-NH2 in which "Fluor" represents 5-carboxyfluorescein conjugated through an amide bond to the peptide containing the sequence PLARRPLPPLP, which is specific for Src SH3 domain binding. This probe had appropriate characteristics and an appropriate saturation curve with the Src protein to (e.g., appropriate Kd and total mP difference on protein binding) to serve as a probe for a competition assay.

Example 8

A FLUORESCENCE-POLARIZATION BASED Src SH2-SH3 DOUBLE BINDING ASSAY

A. Assay—General

Proteins such as Src contain both an SH2 and an SH3 domain. Certain proteins can bind to such SH2- SH3 proteins not through SH2 or SH3 domains alone, but through both domains at once. One example is the protein, p130CAS, which is thought to bind Src via both SH2 and SH3 domains. The SH3 and SH2 binding sequences of p130CAS have been identified by deletional and site-specific mutagenesis (Nakamoto et. al., JBC 271, 8959–8965, 1996). Residues 733–738 (RPLPSP) have been shown to be involved in binding (presumably to the SH3 domain), as has residue Tyr-762 (presumably phosphorylated and responsible for binding Src SH2). Fluorescent probes for FP assays were designed based on these sequences. Such probes can be used in assays that allow simultaneous screening for both SH2-specific and SH3-specific inhibitors. One such probe ("FPC130") is the following:

Fluor-RPLPSPPKFTSQDSPDGQYENSEGGWMEDpYDYVHL domains (for Src SH2) and the SH2-SH3 probe described above (in place of the Src-specific SH2 probe).

B. Saturation Experiments

As in a previous example(s), saturation experiments were performed with fixed concentrations of probe and increasing concentrations of protein (Src-SH2-SH3 in this case).

The Src SH2-SH3 specific probe, FPC130, was synthesized using the techniques described in Example1:

Fluor-RPLPSPPKFTSQDSPDGQYENSEGGWMEDpYDYVHL in which "Fluor" represents 5-carboxyfluorescein conjugated through an amide bond to the peptide containing the sequence PLARRPLPPLP, which is specific for Src Sh3 domain binding (any other fluorescent probe might be substituted). This probe had appropriate characteristics and an appropriate saturation curve with the Src protein to (e.g., appropriate Kd and total mP difference on protein binding) to serve as a probe for a competition assay.

Example 9

A FLUORESCENCE-POLARIZATION BASED HUMAN Src-SH2 BINDING ASSAY USING AN ALTERNATE PROBE

A. Assay—General

A competition assay was developed for Src-SH2 (applicable to any fragment of Src containing the SH2 domain) with a non-fluorescein fluorophore. The fluorophore is one of a family of fluorescent molecules containing the core fluorophore, 4,4-difluoro-4 bora-3a,4a-diaza-s-indacene (commercially available from Molecular Probes Inc.). The structure of the fluorophore-peptide probe is:

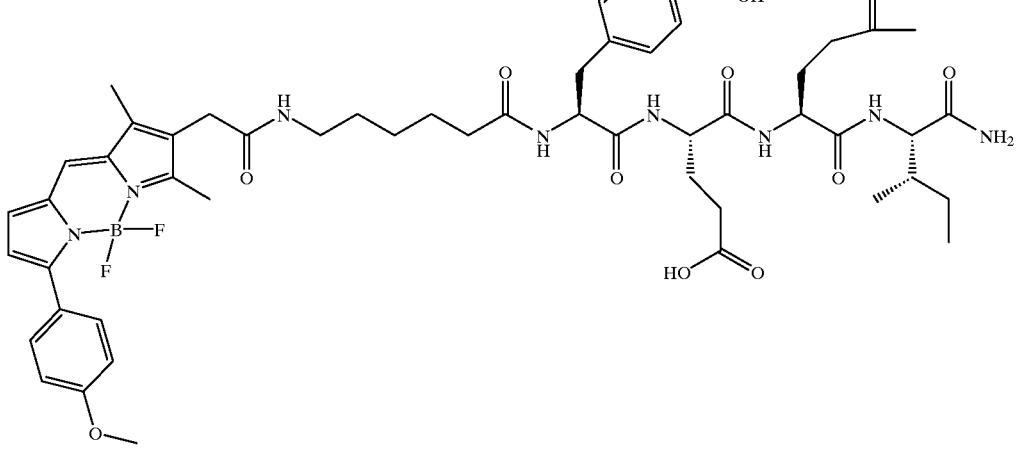

This is the native sequence from p130CAS (733–767). Derivative probes based on the foregoing but using different component SH2 and/or SH3 sequences may be used to vary the affinity or protein specificity, and especially to increase the overall affinity of probe for the desired target protein.

All assay methods, including buffers and instrumental usage, were performed generally as in the case of Src SH2 assay described in Example 4, but substituting a protein containing peptide sequence spanning the Src SH2 and SH3

The fluorophore is BODIPY-TRX, and has spectral characteristics very similar to the Texas Red family of fluorophores. This probe has excitation and emission wavelengths significantly above those of our standard fluorescein probes. Because of these large differences, Bopidy TRX is invisible under standard fluorescein emission conditions, and vice versa. This probe was developed for two primary reasons: first, to allow accurate IC50 measurements of of compounds whose natural fluorescence interferes with our fluorescein based assay (this could include measurements of the fluorescein labeled peptides, as well as natural product extracts and combinatorial compounds.) In addition, the above peptide can be combined with a fluorescein based SH3 probe to run in an assay that will independently test SH2 and SH3 binding at the same time, by reading at different wavelengths.

All assay methods, including buffers and instrumental usage, were performed generally as in the case of Src SH2 assay described in Example 4, but substituting the new probe, shown above, and using different filters on the fluorimeter, to match the spectral characteristics of this alternate probe. Specifically, the excitation/emission filters used with the above are 591/635, compared to 485/530 for fluorescein.

Synthesis of the peptide portion of the probe was as described in Example 1, with production of the peptide NH2-pYEEI. The probe was further synthesized by coupling the free amine peptide, NH2-pYEEI, with the succinimidyl ester of the BODIPY-TRX probe in a 66% DMSO buffer (34% 0.1 MNaBicarbonate). Completion of reaction was monitored by silica gel TLC (4:1:1, butanol, H2O, Acetic Acid solvent system), and was done by 24 hrs. The resultant peptide was quite hydrophobic, and was purified by the same TLC system as just described.

B. Saturation Experiments

As in a previous example(s), saturation experiments were performed with fixed concentrations of probe and increasing concentrations of Src-SH2 protein. The only difference was the use of an alternate set of filters for the red probe, as described in A above.

This probe showed an adequate Kd and total mP difference on protein binding to be a probe for a competition assay.

This invention is not to be limited in scope by the specific embodiments described herein. Indeed, various modifications of the invention in addition to those described herein will become apparent to those skilled in the art from the foregoing description. Such modifications are intended to fall within the scope of the appended claims.

The disclosures of the patents, patent applications and publications cited herein are incorporated by reference in their entireties.

What is claimed is:

1. An in vitro assay method for identifying a test substance which inhibits the mutual association of two molecules, said method comprising:
   (a) providing a first molecule and a second molecule capable of mutual association, said second molecule bearing a covalently linked fluorophore,
   (b) preparing a mixture containing said first and second molecules and at least one test substance,
   (c) irradiating said mixture with polarized light of a suitable wavelength permitting excitation of the fluorophore as indicated by emission of polarized light,
   (d) measuring the degree of polarization of the emission, and
   (e) determining the effect of the presence or concentration of the test substance on the observed emission polarization of the mixture, wherein inhibitory activity of said test substance correlates with decreased depolarization values, and wherein the first molecule comprises a polypeptide which contains at least one receptor domain selected from the group consisting of a Src Homology region ("SH") 2 domain SH3 domain, Phosphotyrosine Interaction domain ("PID") or WW domain.

2. The method of claim 1 wherein the second molecule is a polypeptide.

3. The method according to claim 2 wherein said polypeptide contains at least one SH2 domain or PID, and the second molecule comprises a polypeptide which contains a phosphotyrosine moiety or a phosphotyrosine mimic.

4. The method of claim 3 wherein the polypeptide contains a diflourophosphonophenyl moiety.

5. The method of claim 1 wherein the second molecule is other than a polypeptide.

6. The method of claim 1 wherein the polypeptide contains at least two different receptor domains.

7. The method of claim 1 wherein the polypeptide contains at least two different receptor domains and a ligand designed to bind to at least two of said receptor domains is employed.

8. The method according to claim 1 wherein said one or more of steps (a) through (d) are performed by an apparatus programmed to conduct automatically two or more of said steps for a given test substance or to conduct one or more of said steps for a plurality of test substances or test substance concentrations.

9. The method according to claim 1 where said fluorophore is fluorescein.

10. An in vitro assay method for identifying a test substance which competitively binds to either a receptor tyrosine-phosphorylated peptide and/or its ligand, said method comprising:
   (a) providing (i) a receptor for a tyrosine-phosphorylated peptide, and (ii) a ligand for said receptor, said ligand bearing a covalently linked fluorescent moiety,
   (b) irradiating a mixture containing (i), (ii) and said test substance with polarized light of a suitable wavelength permitting excitation of the fluorophore as indicated by emission of polarized light,
   (c) measuring the degree of polarization of the emission, and
   (d) determining the effect of the presence or concentration of the test substance in decreasing the observed emission polarization of a mixture of (i) and (ii) alone, wherein competitive binding of said test substance correlates with decreased depolarization values.

11. An in vitro assay method for identifying a test substance which inhibits the mutual association of two protein molecules, said method comprising:
   (a) providing a first protein molecule and a second protein molecule capable of mutual association, said second protein molecule bearing a covalently linked fluorophore,
   (b) preparing a mixture containing said first and second protein molecules and at least one test substance,
   (c) irradiating said mixture with polarized light of a suitable wavelength permitting excitation of the fluorophore as indicated by emission of polarized light,
   (d) measuring the degree of polarization of the emission, and
   (e) determining the effect of the presence or concentration of the test substance in decreasing the observed emission polarization of a mixture of said first and second protein molecules in the absence of said test substance.

* * * * *